United States Patent
Dowd et al.

(10) Patent No.: US 9,683,979 B1
(45) Date of Patent: *Jun. 20, 2017

(54) METHOD FOR EXPRESSING PROTEIN QUALITY OF FLOUR

(71) Applicant: General Mills, Inc., Minneapolis, MN (US)

(72) Inventors: Craig A. Dowd, Eagan, MN (US);
James P. Michaels, Blaine, MN (US);
Elliot Augst, Minneapolis, MN (US)

(73) Assignee: General Mills, Inc., Minneapolis, MN (US)

( * ) Notice: Subject to any disclaimer, the term of this patent is extended or adjusted under 35 U.S.C. 154(b) by 20 days.

This patent is subject to a terminal disclaimer.

(21) Appl. No.: 14/936,004

(22) Filed: Nov. 9, 2015

Related U.S. Application Data

(63) Continuation of application No. 14/186,738, filed on Feb. 21, 2014, now Pat. No. 9,207,224.

(60) Provisional application No. 61/767,398, filed on Feb. 21, 2013.

(51) Int. Cl.
| | |
|---|---|
| *G01N 33/10* | (2006.01) |
| *A21D 8/02* | (2006.01) |
| *A23L 1/10* | (2006.01) |
| *G01L 5/00* | (2006.01) |

(52) U.S. Cl.
CPC .............. *G01N 33/10* (2013.01); *A21D 8/02* (2013.01); *A23L 1/1041* (2013.01); *G01L 5/00* (2013.01); *A23V 2002/00* (2013.01)

(58) Field of Classification Search
None
See application file for complete search history.

(56) References Cited

U.S. PATENT DOCUMENTS

| | | |
|---|---|---|
| 3,732,724 A | 5/1973 | Heinz |
| 4,262,024 A | 4/1981 | Mathason |
| 4,311,397 A | 1/1982 | Wright |
| 6,250,147 B1 | 6/2001 | Perten |
| 9,207,224 B1 | 12/2015 | Dowd et al. |
| 2002/0127309 A1 | 9/2002 | Bohlin |
| 2014/0272024 A1 | 9/2014 | Chen |

OTHER PUBLICATIONS

Chandi Gurpreet Kaur et al., (2011), Optimization of Gluten Peak Tester: A Statistical Approach, Journal of Food Duality, 7 pages.
Melnyk, John P. et al., (2011), Effect of the Hofmeister Series on Gluten Aggregation Measured Using a High Shear-based Technique, Food Research International, FRIN-03521, 4 pages.

(Continued)

*Primary Examiner* — Andre Allen
(74) *Attorney, Agent, or Firm* — Christa Head, Esq.; John L. Crimmins, Esq.; Diedericks & Whitelaw, PLC

(57) ABSTRACT

A method for forming a grain composition includes mixing a first grain powder composition with water using a mixing apparatus to form a mixture. Mechanical energy applied to the mixture is calculated from the measured torque. The protein quality is expressed as the measured torque as a function of mechanical energy and is compared to a standard. If the protein quality of the first grain powder composition does not meet the standard, a second grain power composition is formed having a different weight percent of the first source of grain powder than the first grain powder composition.

17 Claims, 23 Drawing Sheets

(56) References Cited

OTHER PUBLICATIONS

Melnyk, John P. et al., (2012), Using the Gluten Peak Tester as a Tool to Measure Physical Properties of Gluten, Journal of Cereal Science (2012) 561-567, 7 pages.

Physical Dough Testing, AACC International Method 54-70.01, (2013), High-Speed Mixing Rheology of Wheat Flour Using the doughLAB, 4 pages.

Physical Dough Tests, AACC International Method 54-21.02, (2011), Rheological Behavior of Flour by Farinograph: Constant Flour Weight Procedure, 8 pages.

Physical Dough Tests, AACC International Method 54-22.01, (2011), Rheological Behavior of Flour by Farinograph: Constant Dough Weight Procedure, 7 pages.

METHOD FOR EXPRESSING PROTEIN QUALITY OF FLOUR

CROSS-REFERENCE TO RELATED APPLICATION(S)

This application is a continuation of U.S. patent application Ser. No. 14/186,738, filed Feb. 21, 2014, which claims priority to U.S. Provisional Patent Application 61/767,398, filed Feb. 21, 2013, which are herein incorporated by reference in their entirety.

TECHNICAL FIELD

The present method relates to a method for expressing protein quality of a grain composition, such as wheat flour. Methods of forming a grain composition and methods of forming dough are also discussed.

BACKGROUND

Wheat flour is a grain powder formed by milling or grinding wheat grain, or simply "wheat." Wheat is typically characterized by protein content, and the price of wheat typically correlates to the protein content, with higher protein wheat typically being sold for a higher price. Similarly, wheat flour is also typically characterized and sold by the protein content. During milling, one or more batches of wheat may be blended together to produce a grain powder with a specified protein content, and thus, a particular manufacturing performance. For example, high-protein wheat may be blended with low-protein wheat to produce a grain powder having a protein content between that of the high-protein wheat and the low-protein wheat.

Wheat flour is a main ingredient in a number of commercially available baked products and ready-to-bake dough, such as refrigerated dough and frozen dough products. Producing consistent and high quality dough and baked products, particularly on a commercial scale, is difficult because of variations in wheat and wheat flour. For example, the amount of water and mixing required for a dough (also referred to as mixing characteristics) may vary by protein, wheat species, growing region, growing season (winter or spring), and grain color (red, white or amber).

Protein has historically been one of the specifications correlated to a dough's mixing characteristic(s) and a dough's manufacturing performance and bake quality in large scale food processing. In the baking industry, Farinographs are often used to characterize the properties of wheat flour. A Farinograph measures and records the torque required to mix a water and flour dough sample over time, and provides the results as a curved graph, known as a Farinogram, having a vertical axis labeled in Brabender Units (BU), an arbitrary unit correlating to the apparent viscosity of the sample, and an horizontal axis labeled in time. The Farinogram can be used to determine the performance characteristics of the flour or dough based on the content of wheat gluten or protein. For example, the Farinogram can be used to estimate the mixing requirements for dough development and the amount of water required for the dough. The Farinograph does not provide a perfect characterization of the dough's potential performance, although it is perhaps the most well known correlation.

Standardized conditions for testing flour with a Farinograph are provided in AACC Method No. 54-21.02, entitled Rheological Behavior of Flour by Farinograph: Constant Flour Weight Procedure, and AACC Method No. 54-22.01, entitled Rheological Behavior of Flour by Farinograph: Constant Dough Weight Procedure. The AACC methods require strict control of conditions, including temperature, are time consuming as multiple runs may be required for one flour sample and the accuracy of the results depend on the skill of the technician reading and interpreting the Farinogram.

SUMMARY

In certain embodiments, a method of expressing a protein quality of a grain powder includes mixing the grain powder and water with a mixing apparatus to form a mixture, measuring the torque applied to the mixing apparatus by the mixture at discrete time intervals, calculating mechanical energy applied to the mixture from the measured torque; and expressing the protein quality of the grain powder as the measured torque as a function of mechanical energy.

In other embodiments, a method for forming a grain composition includes forming a first grain powder composition that includes at least a first source grain powder, mixing at least a portion of the first grain powder composition with water using a mixing apparatus to form a first mixture, measuring the torque applied to the mixing apparatus by the first mixture at discrete time intervals, calculating the mechanical energy applied to the first mixture from the measured torque, expressing the protein quality of the first grain powder composition as measured torque as a function of mechanical energy; comparing the protein quality of the first grain powder composition to a standard, and forming a second grain powder if the protein quality of the first grain powder composition does not meet the standard.

In still further embodiments, a method of forming a dough includes providing a first grain powder having a protein quality, providing a second grain powder having a protein quality, determining the amount of the first grain powder and the amount of the second grain powder from the protein qualities of the first and second grain powders and mixing the determined amounts of the first and second grain powders, water, and at least one dough component to form a dough.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

DETAILED DESCRIPTION

Figure 1:
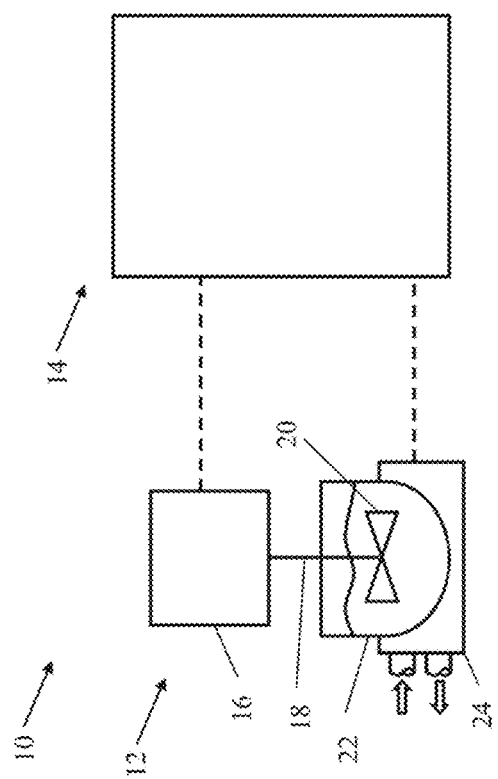
FIG. 1 is a schematic drawing of a mixture evaluation system.

The present disclosure provides a method for characterizing a grain powder composition, such as flour, which can be used in a number of applications. For example, the method for characterizing a grain powder composition described herein may be used to form and/or select grain powder compositions meeting a predetermined specification. As described herein, the characterization can involve characterization or expression of the protein quality of the grain powder composition. In some cases, the grain powder composition may have a lower protein content than what may have been required or expected using previous methods for characterizing grain powder compositions. The method for characterizing a grain powder composition may also be used to characterize the performance characteristics and bake quality of a grain powder for dough production. Based on the performance characteristic(s), one or more processing parameters of the dough production, such as raw material quantities, mixing speed and mixing time, may be adjusted in order to reduce or lower the variability among dough batches.

According to some embodiments of the present method, a grain powder composition, such as flour, is mixed with water to form a mixture. A viscosity factor of the mixture is measured over time during the mixing process, and the viscosity factor as a function of mechanical energy is calculated and/or expressed (e.g., by a data unit) to evaluate a performance characteristic of the grain composition and the mixture.

The grain powder composition may be a composition of one or more grain powders, such as from wheat, rice, millet, maize or a combination thereof, which may have the same or different protein content and/or quality. The grain powder composition may be formed by blending milled grain powders. For example, two or more grain powders having the same or different protein content and/or quality may be blended to form a grain composition. Alternatively, the grain powder composition may be formed by blending grains and then milling to form a composite grain powder. For example, two or more batches of wheat having the same or different protein content may be blended and then milled to form a grain powder composition. In some embodiments, the grain powder composition may have a lower than typically acceptable protein minimum level. Although the methods described herein will be described with respect to wheat flour, one skilled in the art will recognized that other grain powders or flours may also be suitable.

The grain powder composition may be mixed in a bowl using a mixing device, such as a mixer or other mixing apparatus having one or more rotating blades, with a sufficient amount of water to form a dough mixture. As used herein, the term "dough" refers to a paste primarily formed from water and flour, although additional ingredient may also be present, which is sufficiently stiff to knead or roll. Too much water will produce a semi-liquid mixture referred to as a batter and too little water will produce a mixture which separates or crumbles. As described herein, the amount of water and/or flour may be varied so long as the flour is mixed with a sufficient amount of water to achieve a desired apparent viscosity. While the embodiments described herein generally address dough, it is also contemplated that similar methods and devices to those described herein may be applied to a variety of flour and water mixtures.

In some embodiments, the flour and water mixture is mixed in a bowl maintained at a specified temperature, such as by a water bath or other temperature control method. In some embodiments, the bowl is maintained at an ambient temperature, at about 30° C., or at a temperature of less than about 30° C., less than about 20° C., or less than about 16° C. In some embodiments, the flour and water added to the bowl may be at room temperature, e.g., from 20° C. to 23° C., and the bowl may be maintained at a temperature of less than about 20° C. Typically, a Farinogram is run at conditions warmer than 20° C., according to the standard method, to fully elicit the dough performance characteristics of a particular flour. Using a temperature lower than 20° C. is contrary to the established method, but provides a surprising benefit, as described herein.

In some embodiments, the flour and water mixture may be mixed with one or more rotating blades, paddles or other mixing members. In some embodiments utilizing more than one blade, each blade or mixing member of the mixing apparatus may not rotate at the same speed. For example, for a mixing apparatus having a first blade and a second blade, the first blade may rotate at a higher speed (e.g., at a higher rotations per minute) than the second blade. The mixing speeds described herein will describe the mixing or rotational speed of the slowest mixing member for mixing apparatuses having two or more mixing members.

In some embodiments, the flour and water mixture may be mixed using a mixing apparatus at a speed of 70 revolutions per minute (RPM) or less, or 100 RPM or less. In other embodiments, the flour and water mixture may be mixed using a mixing apparatus at a speed of 100 RPM or greater or 1000 RPM or greater. In some embodiments, suitable mixing speeds when the mixing bowl is maintained at a temperature below 30° C., 20° C., or 16° C. includes at below 70 RPM, below 100 RPM, above 100 RPM and above 1000 RPM. In some embodiments, suitable mixing speeds when the mixing bowl is maintained at a temperature of at or above 30° C. includes above 100 RPM and above 1000 RPM.

Mixing the flour and water mixture (e.g., the dough) in the bowl may create heat due to, for example, heat generated by frictional forces between the dough and bowl and the heat of hydration (e.g., the energy released when the flour absorbs the water). During mixing, the dough will reach a constant or steady state temperature. In some embodiments, the steady state temperature of the dough is less than or equal to the average temperature of the flour and water added to the bowl. As described herein, the temperature of the bowl and the temperature of the water and flour may be controlled to control the height and/or formation of a hydration peak. As used herein, "hydration peak" refers to a peak or local maximum in the dough's apparent viscosity prior to the dough achieving maximum development, where apparent viscosity is the inverse of the dough's mobility.

A non-Newtonian fluid, such as a wheat flour and water dough, is a fluid in which shear stress is not directly proportional to deformation rate. Non-Newtonian fluids may be characterized by apparent viscosity, which is defined by the relationship between sheer stress and shear rate.

During mixing, the apparent viscosity of the dough will increase until the dough reaches maximum development after which the apparent viscosity of the dough will decrease as the gluten bonds of the dough begin to break down. As used herein, the term "development peak" refers to the dough's maximum development, and the term "peak time" refers to the time required to reach the development peak.

A viscosity factor of the dough is measured over time during mixing. That is, a plurality of viscosity measurements may be made during mixing. The viscosity factor indicates either directly or indirectly the viscosity of the dough. Suitable viscosity factors include the apparent viscosity of the mixture and the torque or force on the mixing device to mix the mixture. Suitable viscosity factors also include torque as a percent of the maximum or peak torque measured during mixing (also referred to as torque as a percent of peak) and apparent viscosity as a percent of the maximum or peak apparent viscosity measured during mixing (also referred to as apparent viscosity as a percent of peak).

The mixture may be mixed at least until the development peak is reached. In some embodiments, the viscosity factor of the dough as function of time is measured from a time before the development peak to a time after the development peak. The viscosity factor may be measured for a predetermined time after peak development, such as 3, 5 or 10 minutes after peak development.

The viscosity factor as a function of mechanical energy can be calculated. Mechanical energy may be determined by integrating the work required for mixing (e.g., torque or force) over time, and may be expressed per unit mass or as specific mechanical energy. The viscosity factor as a function of mechanical energy may be a suitable performance characteristic for evaluating a mixture or flour. For example, as described herein, apparent viscosity as a percent of peak apparent viscosity as a function of mechanical energy provides a reliable indication of at least one performance characteristic of a mixture and/or flour.

FIG. 1 is a schematic drawing of a mixture evaluation system 10, according to some embodiments. As shown, the system includes a test or mixing apparatus 12 and a data unit 14. In some embodiments, the mixture evaluation system 10 is a bench or laboratory testing apparatus. In other embodiments, the mixture evaluation system 10 forms part of a manufacturing line.

In some embodiments, the test apparatus 12 includes a motor assembly 16, a drive shaft 18, a mixing member 20, a mixing receptacle 22, such as a bowl, and a receptacle temperature control unit 24. The motor assembly 16 optionally includes a feedback sensor (not shown) for sensing motor power (power is current multiplied by voltage), drive shaft speed, or other feedback variable to be used in evaluating torque on the drive shaft 18 during mixing. The motor assembly 16 is connected to a power source (not shown) and includes motor control circuitry, sensors, and additional or alternative features as desired. The drive shaft 18 interconnects the motor assembly 16 and the mixing member 20. As described below, where the test apparatus 12 is a Farinograph system, the mixing member 20 optionally includes two rotatable blades.

In some embodiments, the mixing receptacle 22 is configured to receive a dough mixture such that the mixing member 20 is able to interact with, or mix, the dough mixture. The receptacle temperature control unit 24 is configured to control the temperature of the mixing receptacle 22 and thus the temperature of the dough mixture in the receptacle 22. In some embodiments, the receptacle temperature control unit 24 includes a circulation system for circulating water, coolant, or other fluid to raise or lower the temperature of the mixing receptacle 22 to a desired mixing temperature.

The data unit 14 is connected directly or indirectly, via a wired or wireless connection, to the test apparatus 12. The data unit 14 includes hardware, software, and/or firmware specifically configured to execute the methods for determining performance characteristics in the following description. Instructions and other information relating to various methods described herein are stored on a computer readable media as desired. The data unit 14 is optionally limited to a single location (e.g., a single work station) or includes a plurality of networked devices in geographically separated regions operated by one or more users as desired.

As shown schematically in FIG. 1, the data unit 14, also described generally as a processor, includes hardware, firmware, and or software configured to receive sensed information from the test apparatus 12 (e.g., torque and the temperature of mixing receptacle 22) and to control test apparatus operation parameters (e.g., mixing member rotation speed and mixing receptacle temperature) as desired.

In some embodiments, the mixture evaluation system 10 includes a Farinograph unit, such as a Farinograph E, or a Brabender GlutoPeak. The Farinograph E and the GlutoPeak are both available from C.W. Brabender Instruments, Inc., South Hackensack, N.J. A Farinograph generally includes two rotating blades for mixing the flour and water mixture. The resistance of the dough against the blades creates a force or torque on the blades. As the apparent viscosity of the dough increases, the torque on the blades also increases. A Farinograph receives a signal representing the force, torque or apparent viscosity in Brabender Units and records this as a function of time during the mixing process. The apparent viscosity and the mechanical energy can be calculated from the Farinograph data, and the apparent viscosity as a function of mechanical energy can be determined. As described below, the following methods for determining performance characteristics and associated graphs and displays are optionally accomplished by the mixture evaluation system 10, such as a Farinograph device with software, firmware, and/or hardware configured to receive test data (e.g., torque signals) and generate a desired output (e.g., test graphs and/or performance characteristic values).

Figure 2:
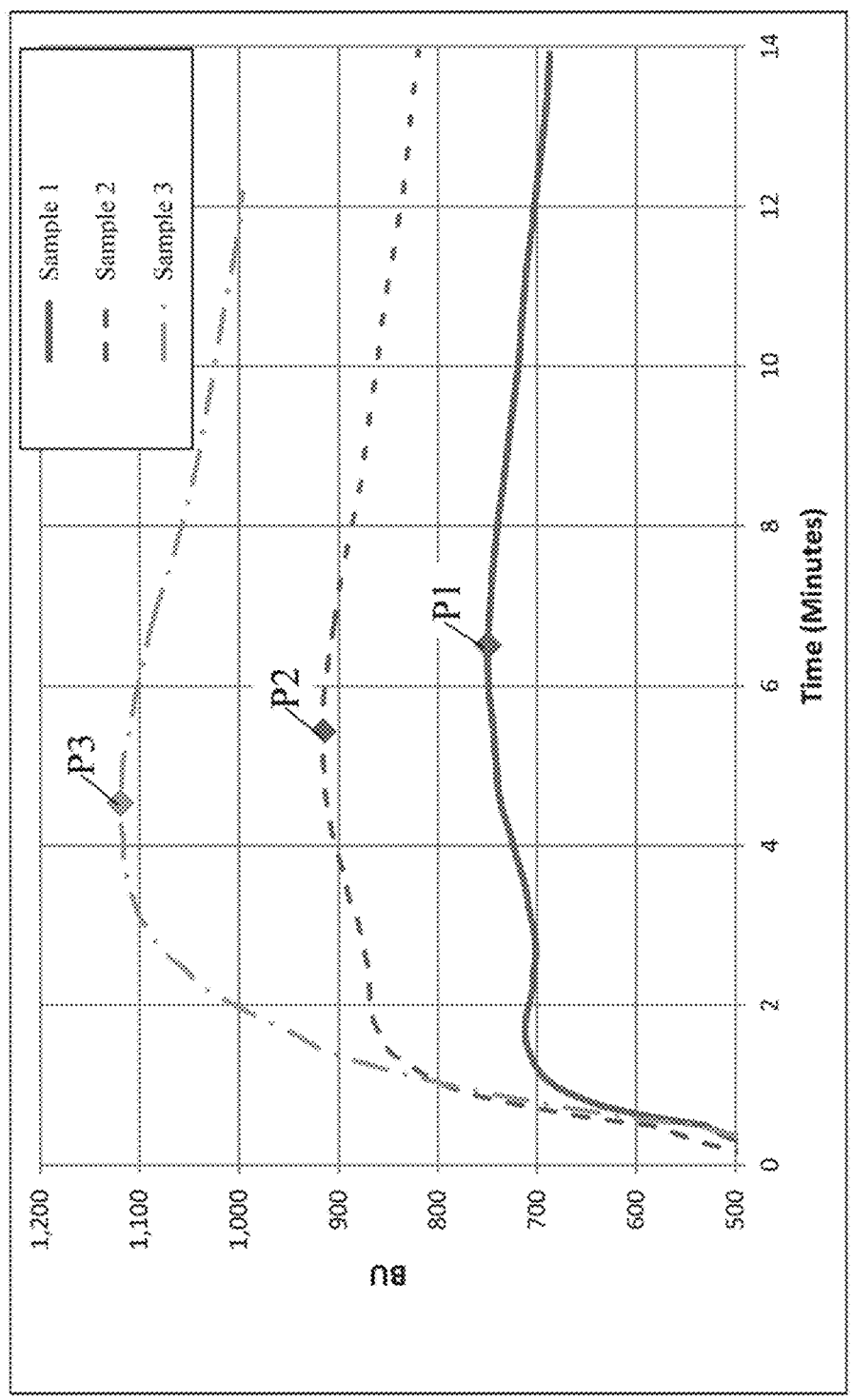
FIG. 2 illustrates a viscosity factor as a function of time for samples.

FIG. 2 is a graph of apparent viscosity (in Brabender Units (BU)) versus time (in minutes) for three dough samples made with the same flour and the same total amount of flour and water but having different flour to water ratios. The dough samples were tested in a Farinograph with a bowl temperature of 15.6° C. (60° F.) and at a mixing speed of 63 RPM. Sample 1 had a flour to water ratio of 1.6 and a maximum apparent viscosity of 750 BU; Sample 2 had a flour to water ratio of 1.7 and a maximum apparent viscosity of 916 BU; and Sample 3 had a flour to water ratio of 1.8 and a maximum apparent viscosity of 1120 BU. The maximum apparent viscosity increased with increasing flour to water ratio.

The development peak for Samples 1, 2 and 3 are labeled P1, P2 and P3, respectively, in FIG. 2. The development peak of each sample occurred at the maximum apparent viscosity measured. That is, the dough of each sample reached its maximum development at the maximum apparent viscosity. Each sample reached the development peak at a different mix time. For example, Sample 1, which had the lowest flour to water ratio, reached its development peak after approximately 6.5 minutes of mixing, while Sample 3, which had the highest flour to water ratio, reached its development peak in less time, after approximately 4.5 minutes of mixing.

Figure 3:
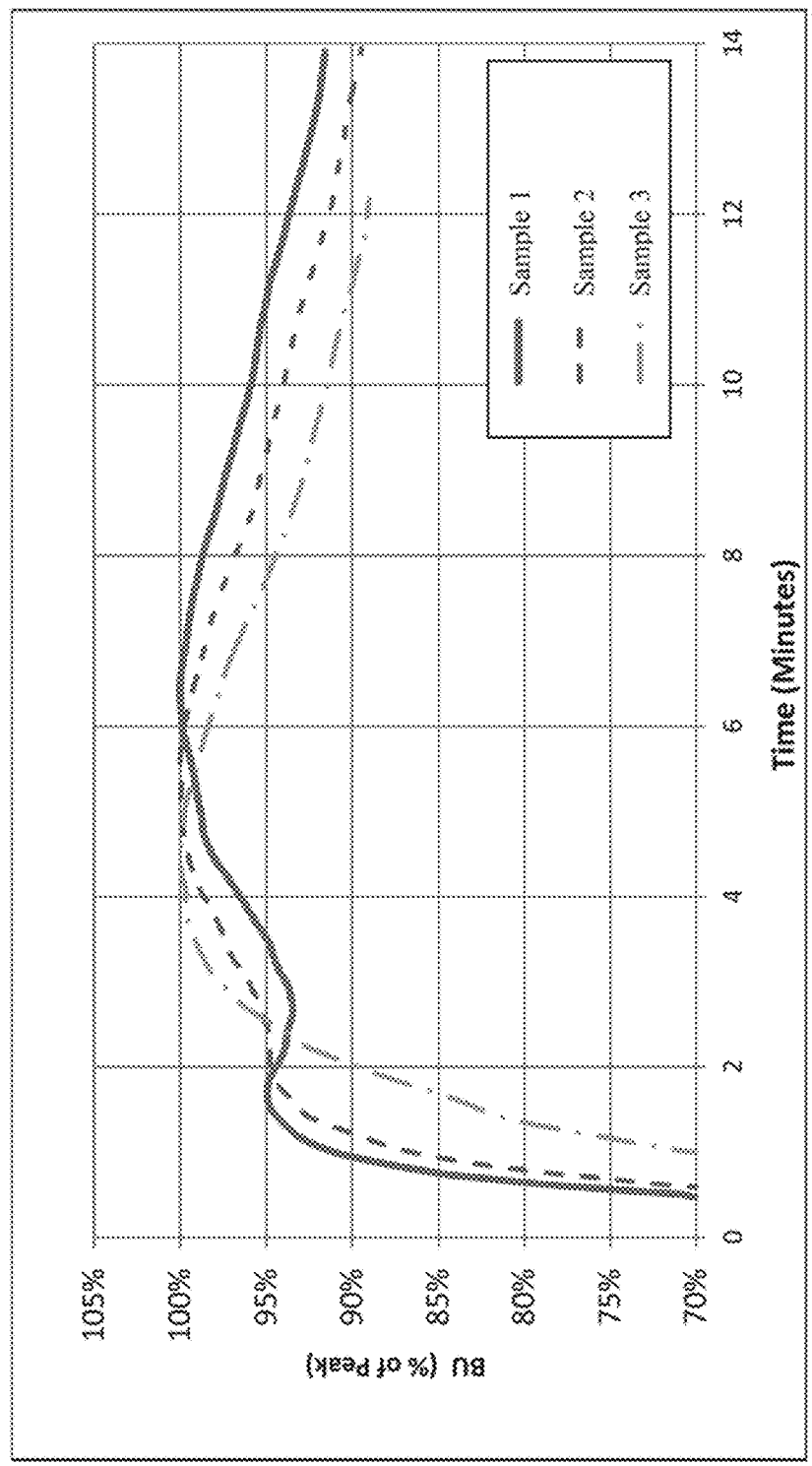
FIG. 3 illustrates an alternative viscosity factor as a function of time for the samples of FIG. 2.

FIG. 3 is a graph of apparent viscosity as a percent of peak versus time (in minutes) for the three dough samples of FIG. 2. Similar to FIG. 2, the development peak for each sample is at the maximum apparent viscosity. However, because the y-axis is presented as apparent viscosity as percent of peak, the peak development occurs at 100% peak apparent viscosity for each sample.

Figure 4:
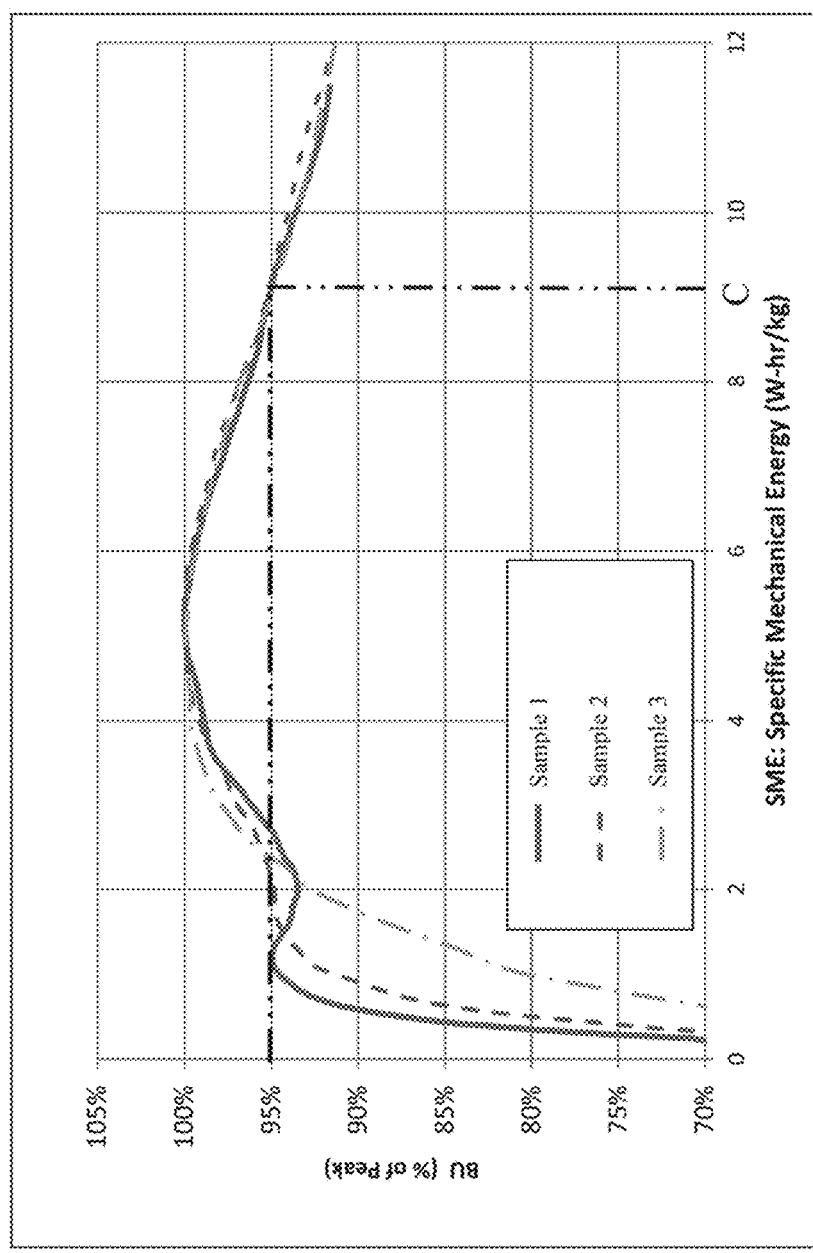
FIG. 4 illustrates a viscosity factor as a function of mechanical energy for the samples of FIG. 2.

Specific mechanical energy is calculated by integrating torque over the mix time. FIG. 4 is a graph of apparent viscosity as a percent of peak versus specific mechanical energy (in W-hr/kg). It has been found that when the x-axis is transformed to mechanical energy instead of time (as in FIG. 2) and the y-axis is transformed to apparent viscosity as a percent of peak, the development peak of the dough is independent of the flour to water ratio. Said another way, dough of the same flour requires the same amount of specific mechanical energy to reach the development peak regardless of the flour to water ratio of the dough, within a reasonable flour to water ratio range. When the x-axis is transformed to mechanical energy and the y-axis is transformed to apparent viscosity as a percent of peak, the post-peak behavior of the dough is also independent of the flour to water ratio as seen in the alignment of Samples 1, 2 and 3 following peak.

In some embodiments, the flour may be characterized by the maximum apparent viscosity measured during mixing. For example, Sample 1 may be characterized as having a maximum apparent viscosity of 750 BU, Sample 2 may be characterized as having a maximum apparent viscosity of 916 BU and Sample 3 may be characterized as having a maximum apparent viscosity of 1120 BU. In some embodiments, this characterization may be considered an expression of the protein quality.

Additionally or alternatively, the flour may be characterized by the mechanical energy at a predetermined percent of peak apparent viscosity following the development peak, such as at less than about 100%, at less than or equal to about 98%, or at less than or equal to about 95% of peak apparent viscosity after the development peak. For example, the samples may be characterized by the mechanical energy at 95% peak apparent viscosity following the development peak, which is indicated by "C" in FIG. 4. As described herein, the post-peak behavior (e.g., the behavior of the dough after the development peak) of Samples 1, 2 and 3 are similar. As shown in FIG. 4, Samples 1, 2 and 3 each have a performance characteristic "C" of about 9.2 W-hr/kg, where "C" is the mechanical energy at 95% of peak apparent viscosity following the development peak.

The current method may be used for selecting the grain powder composition of a grain powder. As previously described, grains and grain powder compositions, such as flour, traditionally have been characterized by protein content, which is not always an accurate indicator of the performance characteristics of a dough formed with a specified grain powder composition. There are some grains and grain powder compositions which might perform adequately which do not meet the minimum protein specification. While not wishing to be bound by theory, it is believed that performance characteristics of dough, such as the amount of water and mixing required, are influenced by the protein quality of the flour, and not necessarily by protein amount. Using the current method, a performance characteristic may be evaluated for a given grain composition without reference to the protein content of the grain composition. Rather, using the current method, a grain composition may be evaluated with reference to the functionality of the protein (or protein quality) during mixing. In some embodiments, a first mixture may be formed by mixing a first grain powder or flour with water and evaluating the performance characteristic. The performance characteristic may be compared to a predetermined specified range to determine whether the performance characteristic falls within the specified range. The flour may be accepted if the performance characteristic falls with the specified range.

In some embodiments, the first flour may be blended with one, two or more grain powders or flours which may have the same or different protein contents. For example, the first flour may be blended with a second grain powder or flour having a protein content different than that of the first. It has been found that a higher protein may generally increase the performance characteristic of a flour, and the amount of the second flour may be adjusted to produce a blended grain powder or flour composition having a performance characteristic that falls within the predetermined specified range. For example, if the performance characteristic of the first flour exceeds or is above the predetermined specified range, a second flour having lower protein content than the first may be blended with the first flour to form a blended flour composition. The amount of the lower-protein flour may be increased until the performance characteristic of the resulting blended flour composition falls within with the specified range. The amount of the lower-protein flour may be decreased if the performance characteristic of the resulting blended flour composition falls below the predetermined specified range.

Similarly, if the performance characteristic of the first flour is below the predetermined specified range, a second flour having a higher performance characteristic can be blended with the first flour to produce a blended grain composition with a performance characteristic that falls within the specified range. In some embodiments, the second flour may have a higher protein content.

The specified range for the performance characteristic may be predetermined by determining the performance characteristic for grain powder compositions or flours that produce acceptable dough. For example, the specified range may be predetermined based on the performance characteristic of one or more samples which produced acceptable dough under specified processing conditions.

By specifying the performance characteristic of the flour rather than the protein content, the current method enables lower cost materials (e.g., grain powders and flours) to be maximized in the blended compositions while still providing blended compositions having suitable performance properties to be used in dough and baked products. Further, grain compositions formed by the current method may have suitable properties for dough while having a lower protein content than specified under previous standards.

In some embodiments, the current method can include a computerized method for evaluating a performance characteristic of a water and grain powder mixture. For example, the mixture evaluation system 10 is optionally used with a water and flour mixture that is mixed with the test apparatus 12. In some embodiments, the test apparatus 12 measures the torque during mixing and the torque measurement is provided to the data unit 14, where the data unit 14, or processor, is specifically configured to receive and interpret the torque measurement supplied during mixing. For example, the torque measurement signal may be generated by measuring the force of the mixture on the mixing member 20 using one or more sensors associated with the test apparatus 12 and/or data unit 14.

Figure 5:
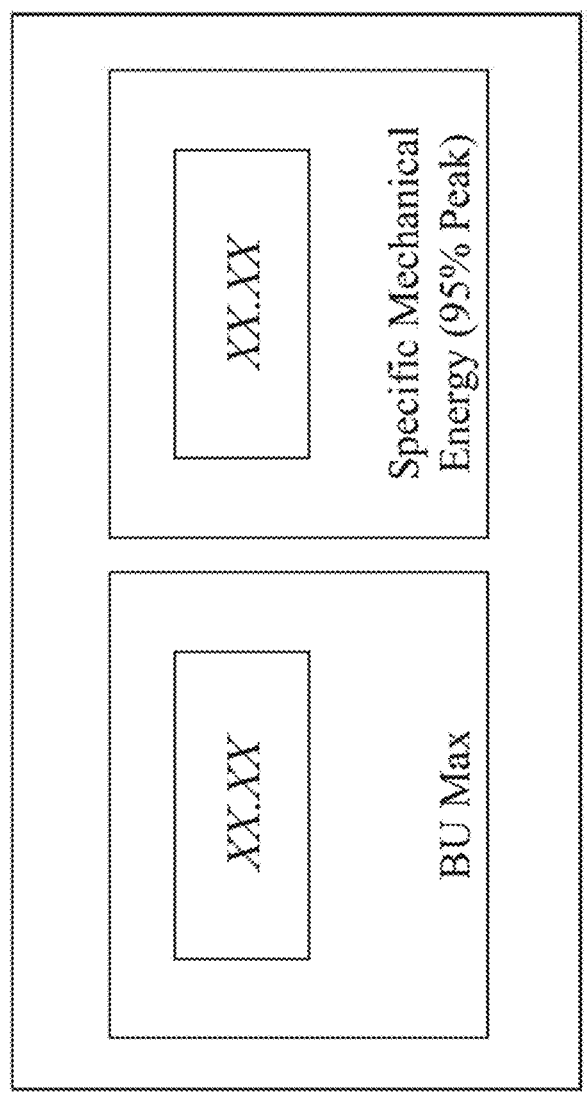
FIG. 5 shows an output according to some embodiments.

In some embodiments, using the torque measurement signal, the data unit 14 employs software (e.g., spreadsheet software incorporating previously defined formulas and data fields), firmware, and/or hardware, to calculate a viscosity factor and the mechanical energy of the mixture. One or more performance characteristics of the mixture may be determined based on the viscosity factor as a function of mechanical energy and may be outputted. As described herein, suitable viscosity factors include torque, apparent viscosity and apparent viscosity as a percent of peak apparent viscosity. Mechanical energy may be outputted in terms of energy or in terms of energy per mass unit (specific mechanical energy). The performance characteristic may be outputted in a variety of forms, including on a display, such as a digital display, in an electronic file, or provided in a non-electronic form, such as a printed output. For example, FIG. 5 shows an output according to some embodiments, where the performance characteristics of maximum BU and specific mechanical energy at 95% peak apparent viscosity after the development peak have been calculated by the data unit 14 and displayed on a monitor associated with the test unit 14. In some embodiments, suitable performance characteristics may also be outputted as maximum torque or maximum apparent viscosity.

In other embodiments, the current method can be used to characterize the performance of a flour used in a dough product. One or more dough processing conditions may be adjusted during dough production based on the one or more performance characteristics. As described herein, flour may be used in dough prepared for baked goods and ready-to-use dough products. To form the dough, flour, water and optional additional ingredients are mixed together under specified processing conditions, such as mix time, mix speed and temperature. It is desirable that the resulting dough has consistent or uniform properties, even if there are variations in the raw materials, such as the flour.

Previously, flour was characterized with a Farinograph using AACC standardized methods 54-21.02 and/or 54-22.01. The method described herein differs from AACC methods in several ways. First, the method described herein provides a performance characteristic by calculating the viscosity factor as a function of mechanical energy.

Further, in some embodiments, the performance characteristic is provided as a viscosity factor as a function of mechanical energy in which the viscosity factor is apparent viscosity as a percent of peak apparent viscosity. When the performance characteristic is defined in this way, the development peak and the post-peak behavior of the dough is independent of the flour to water ratio so long as there is a sufficient amount of water to form a dough.

There is no requirement that the development peak produced by the current method occur at a specified viscosity factor. For example, the current method provides reliable results when development peak occurs at 500 BU (as required by the AACC methods), above 500 BU and below 500 BU. The current method provides accurate and reliable results regardless of the location of the development peak, saving time by eliminating the need to redo samples because the development peak occurs outside of specified parameters.

In the current method, the mixing receptacle or bowl may be cooled. For example, the bowl may be maintained at less than 20° C. or less than 16° C. It has been found that maintaining the bowl at a temperature such that the steady state temperature of the dough is equal to or less than the average temperature of the water and flour added to the bowl prevents the hydration peak from occurring at a higher apparent viscosity than the development peak when mixing at a speed below 100 RPM or below 70 RPM. Using the current method, the development peak may be the highest peak (e.g., may occur at the highest viscosity factor), which reduces training time for operators, improves the precision of the results and allows the development peak to be automatically identified, such as by a processor or computer software.

Although the above description describes analysis of a grain powder composition (e.g., flour) and water mixture, any suitable liquid may be mixed with the flour for the analysis. For example, when the mixture evaluation system is a Brabender GlutoPeak, the analysis liquid may be $CaCl_2$.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Example 1

The post-peak behavior as an indication of flour properties was investigated by adding increasing amounts of hard red spring wheat flour to hard red winter wheat flour. Sample 4 included 0%, Sample 5 included 40%, Sample 6 included 60% and Sample 7 included 100% hard red spring wheat. Each sample was tested at the same flour to water ratio.

Figure 6:
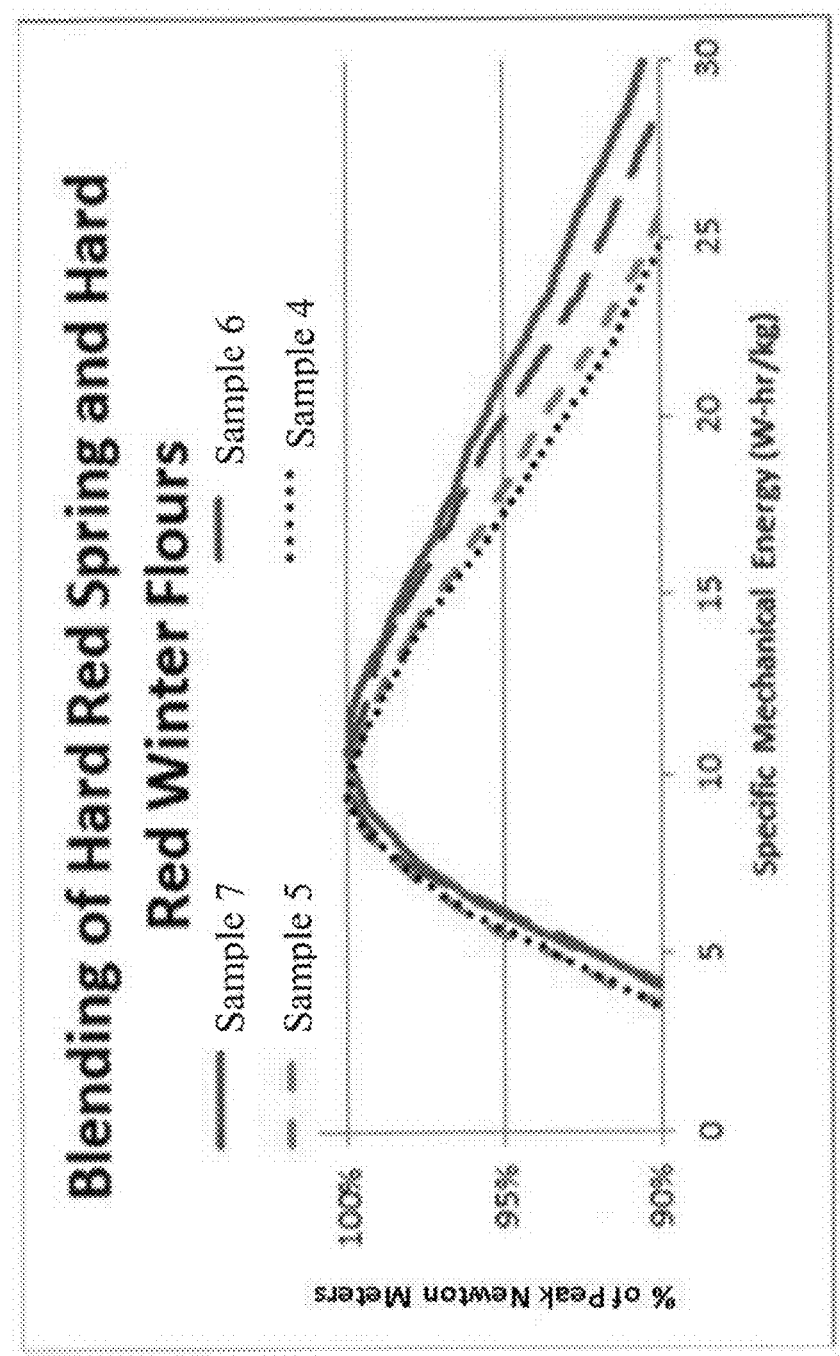
FIG. 6 illustrates a viscosity factor as a function of mechanical energy for samples.

The bowl temperature of a Farinograph E available from C.W. Brabender Instruments, Inc., South Hackensack, N.J., was set to 15.6° C. To ensure proper temperature, the temperature of the bowl was observed at the set temperature for at least 10 minutes prior to each run. The Farinograph and commercially available software package for the recordation and production of a Farinogram were started and the flour and water were added to the bowl of the Farinograph. The same amount of flour and water were added for each run. The water was added in a sufficient amount so that a dough was formed for each run. The Farinograph was set to a mixing speed of 63 RPM. The Farinograph includes two mixing paddles which operate at different speeds. When the Faringraph is set at a mixing speed of 63 RPM, one paddle rotates at 63 RPM and the other paddle rotates at 94.5 RPM. Each run was allowed to run to completion. That is, each run was allowed to run at least until the peak development was reached. Following the test, the mean Farinograph was filtered to smooth the data and the apparent viscosity (in Newton-meters) or Brabender Units (as a % of peak) as a function of specific mechanical energy (SME) (in W-hr/kg) was calculated. FIG. 6 presents the results for each wheat mixture (0% (Sample 4), 40% (Sample 5), 60% (Sample 6) and 100% (Sample 7) by weight hard red spring wheat).

For each sample, the development peak occurs at apparent viscosity of 100% of peak, where peak is equivalent to the highest measured apparent viscosity in each respective run.

The post-peak curve or behavior varied by sample. For example, the post-peak curve had a steeper slope (e.g., dropped further) when the wheat mixture included a greater amount of hard red winter flour. Thus, the post-peak curve behavior may be indicative of the properties of the wheat mixture.

Figure 7:
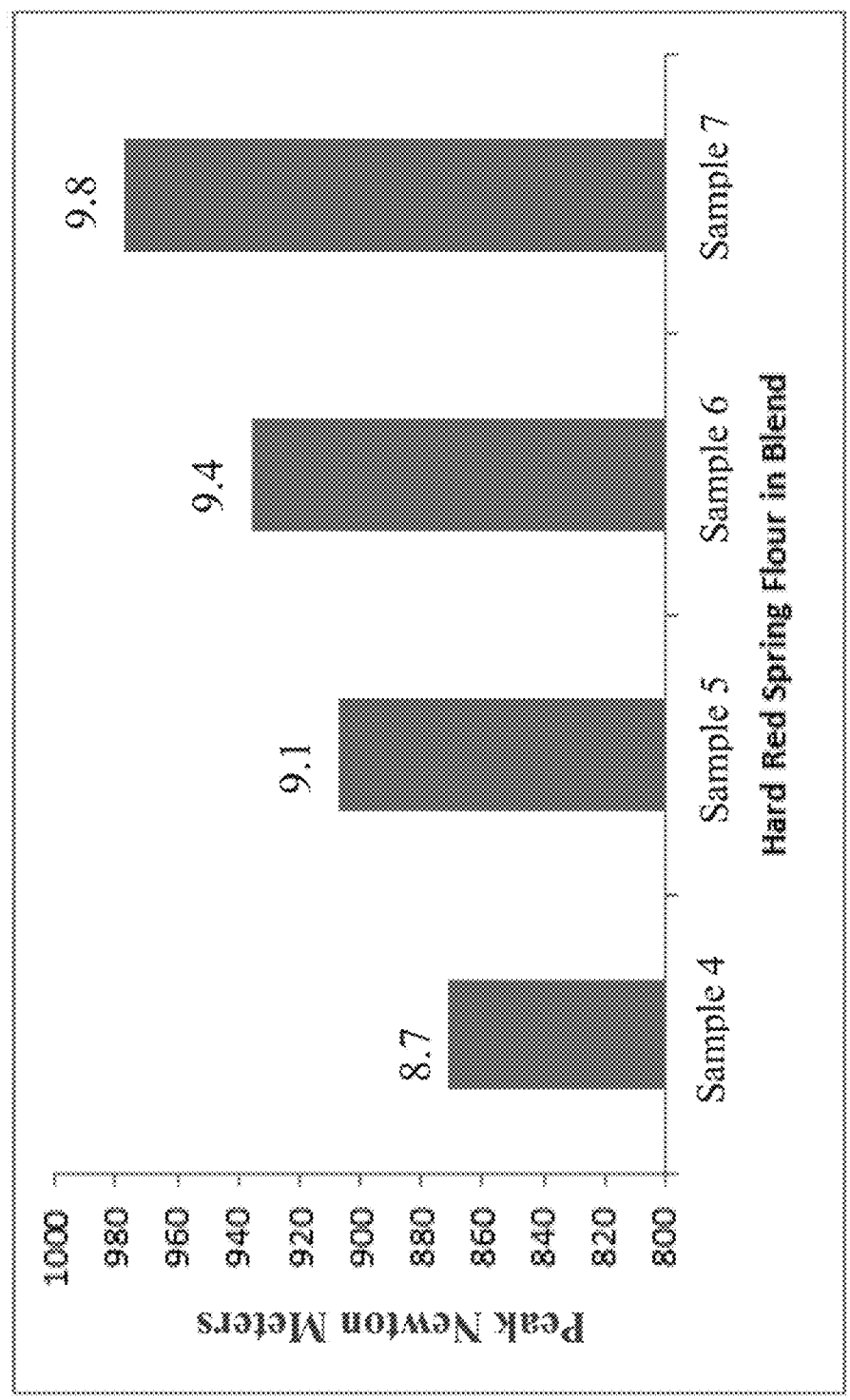
FIG. 7 illustrates the peak Newton-meters for each sample of FIG. 6.

FIG. 7 illustrates the peak Newton-meters for each sample. The peak Newton-meters increased as the amount of hard red spring flour increased.

Figure 8:
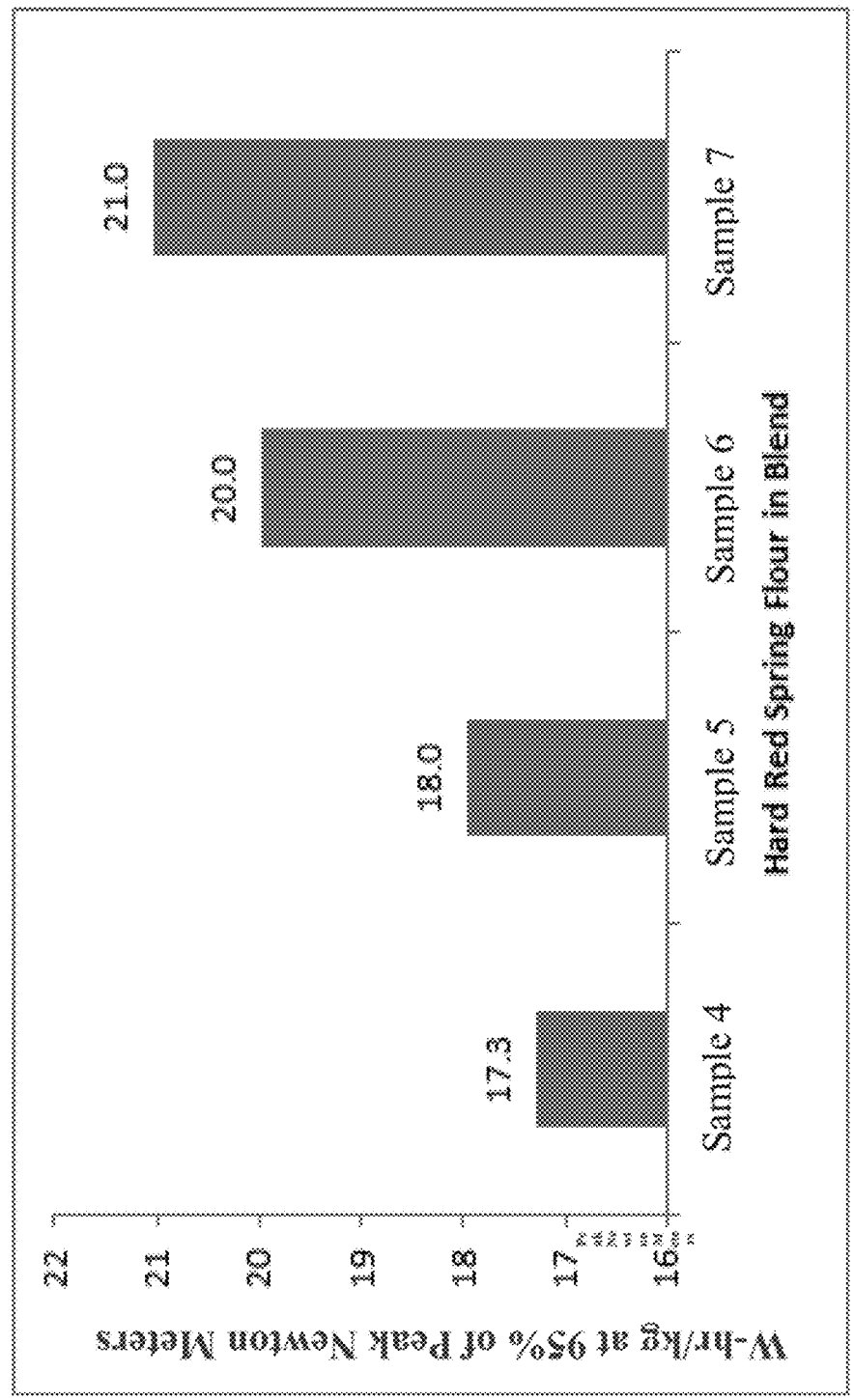
FIG. 8 illustrates the specific work energy for each sample of FIG. 6.

FIG. 8 illustrates the specific work energy at 5% drop from peak Newton-meters for each sample. The specific work energy at 5% drop from peak Newton-meters increased as the amount of hard red spring flour increased, indicating that the post-peak curve behavior may be indicative of the properties of the wheat mixture.

Example 2

The mixing conditions suitable for determining a protein quality or protein characteristic of a flour composition were investigated by changing the mix speed and the temperature at which the mixing bowl was maintained during the mixing process using either a Farinograph E or a GlutoPeak.

The compositions of Samples 8, 9, 10 and 11 are provided in Table 1. The samples used the same flour but different flour to water ratios. Samples 8-11 were mixed with the Farinograph E as described above for Samples 4-7, at a mixing speed of 63 RPM. The mixing bowl of the Farinograph E was maintained at 15.6° C. during the mixing process.

TABLE 1

|  | Flour (grams) | Water (grams) |
| --- | --- | --- |
| Sample 8 | 316 | 164 |
| Sample 9 | 309 | 171 |
| Sample 10 | 302 | 178 |
| Sample 11 | 295 | 185 |

Figure 9:
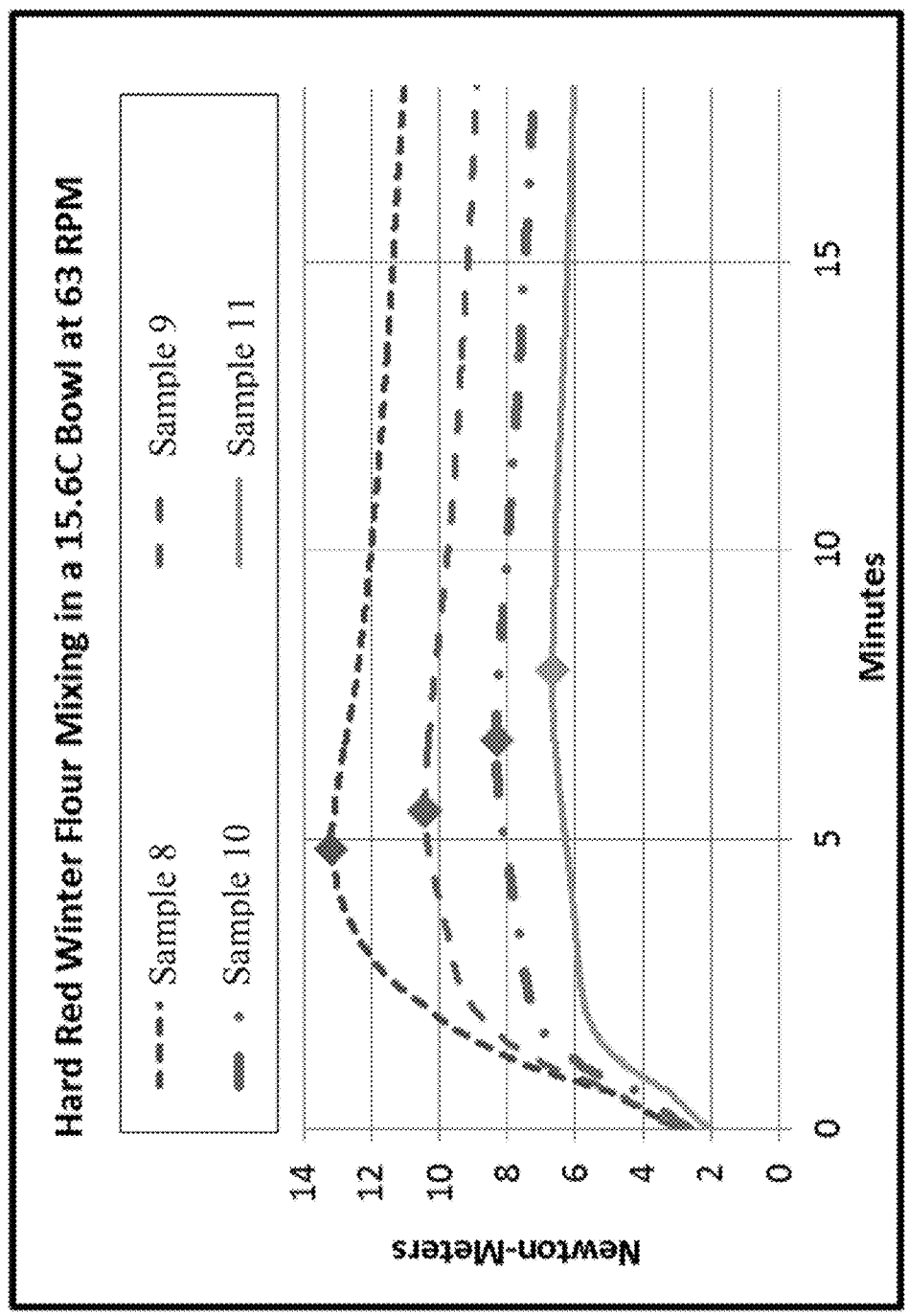
FIGS. 9-23 illustrate a viscosity factor as a function of time, a viscosity factor as a function of mechanical energy or an alternative viscosity factor as a function of mechanical energy for samples

FIG. 9 is a graph of apparent viscosity (in Newton-meters) versus time (in minutes) for Samples 8-11. As illustrated in FIG. 9, the maximum apparent viscosity increased with increasing flour to water ratios.

Figure 10:
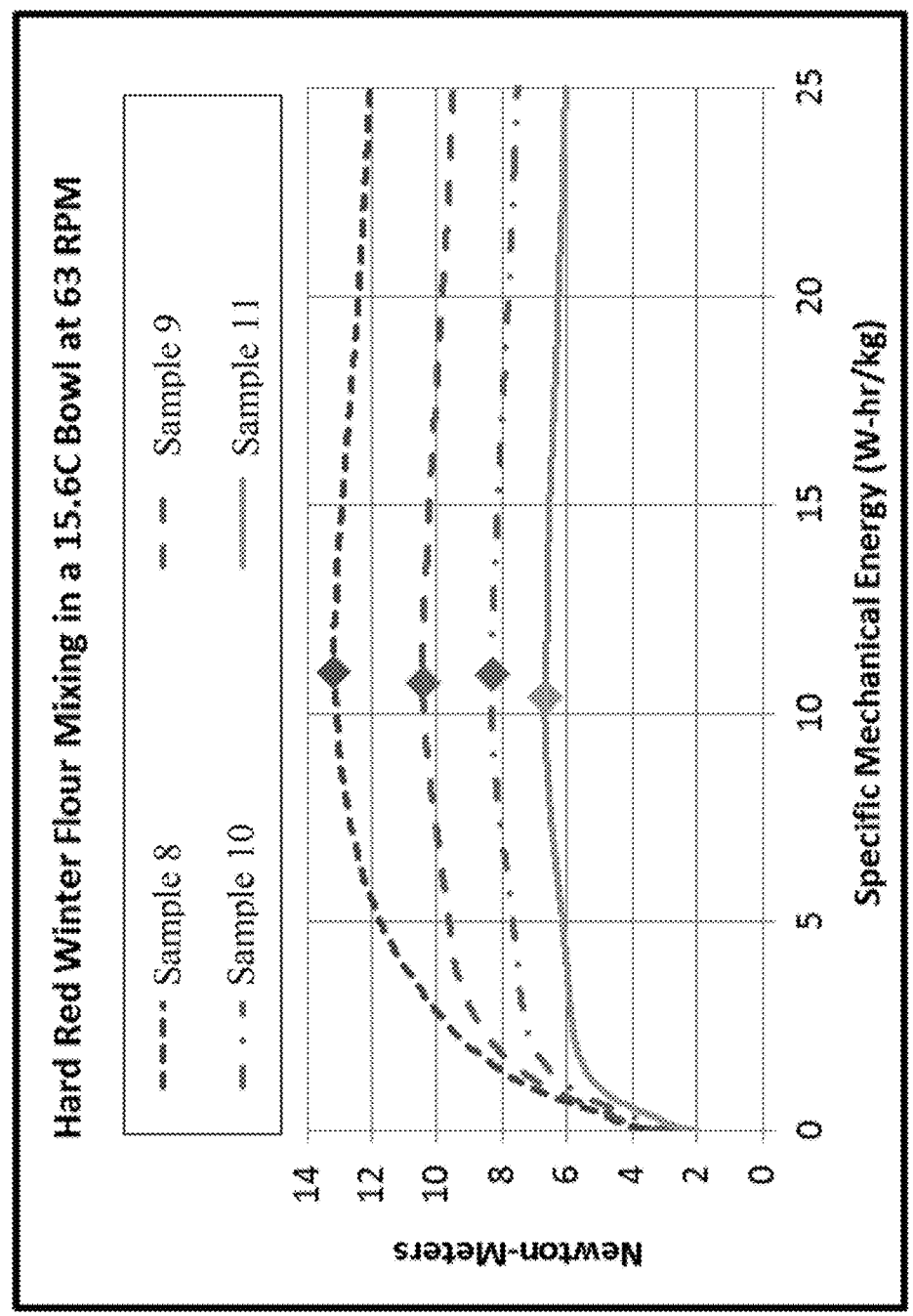

FIG. 10 is a graph of apparent viscosity versus specific mechanical energy for Samples 8-11. Similar to FIG. 9, the development peak for each sample is at the maximum apparent viscosity.

Figure 11:
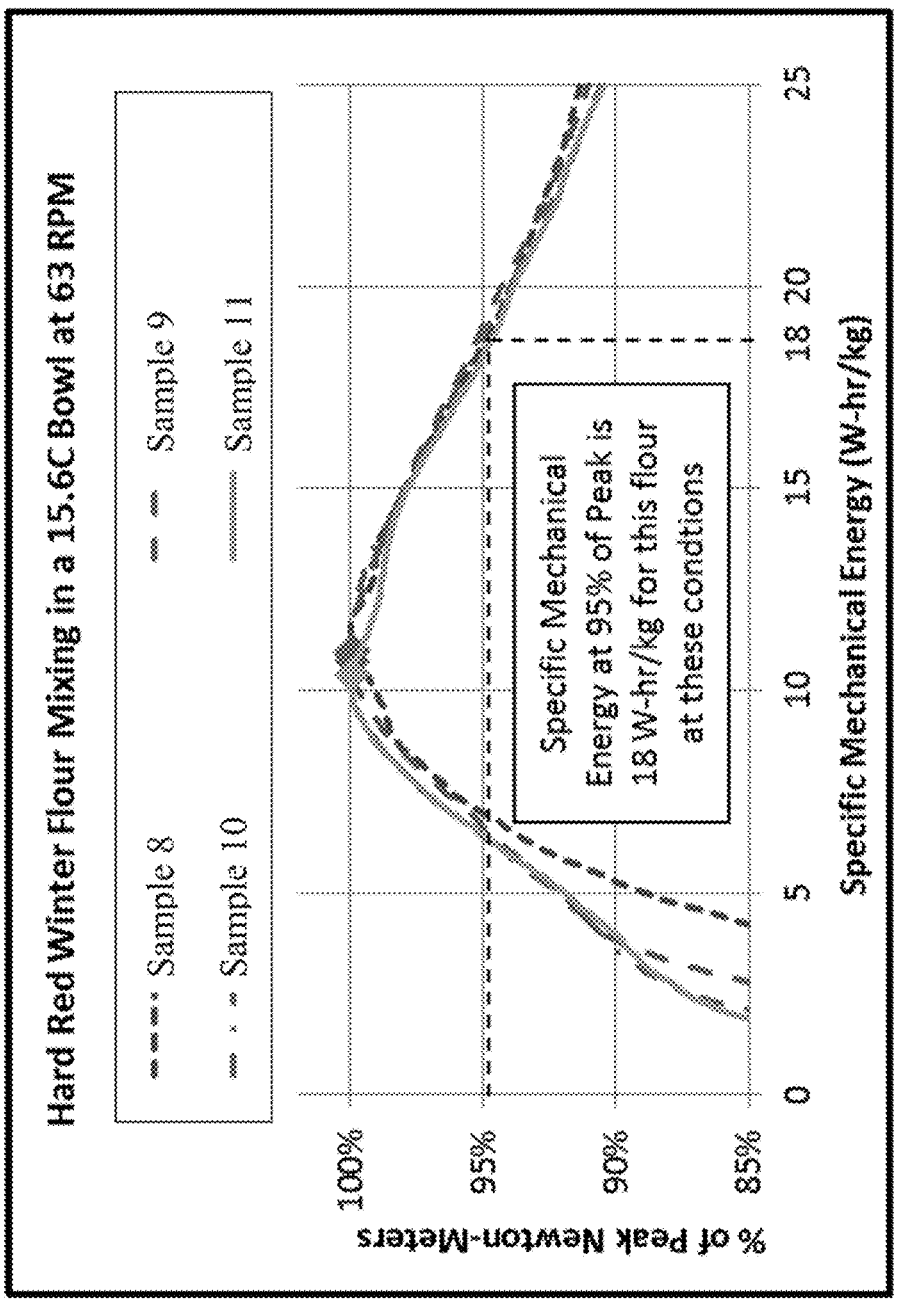

FIG. 11 is a graph of apparent viscosity as a percent of peak versus specific mechanical energy (in W-hr/kg) for Samples 8-11. As illustrated in FIG. 11, when the x-axis is transformed to mechanical energy instead of time (as in FIG. 9) and the y-axis is transformed to apparent viscosity as a percent of peak, the development peak of the dough is independent of the flour to water ratio.

Similar to Samples 8-11, Samples 12-14 used the same flour but at different flour to water ratios as summarized in Table 2. Samples 12-14 were mixed with a Farinograph E as describe above for Samples 4-7 at a mixing speed of 120 RPM. The mixing bowl of the Farinograph E was maintained at 15.6° C. during the mixing process.

TABLE 2

|  | Flour (grams) | Water (grams) |
| --- | --- | --- |
| Sample 12 | 300 | 180 |
| Sample 13 | 293 | 187 |
| Sample 14 | 286 | 194 |

Figure 12:
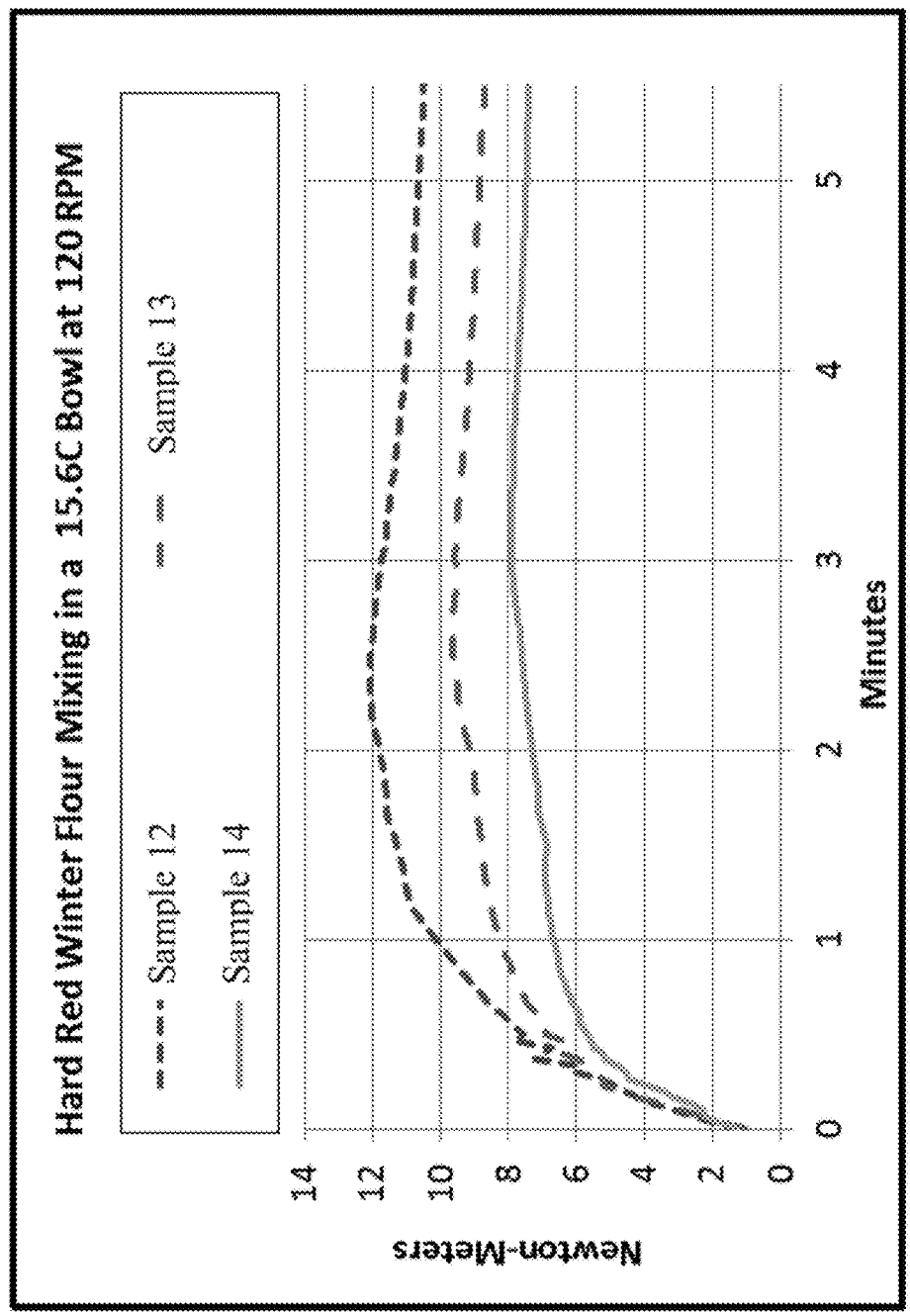
Figure 13:
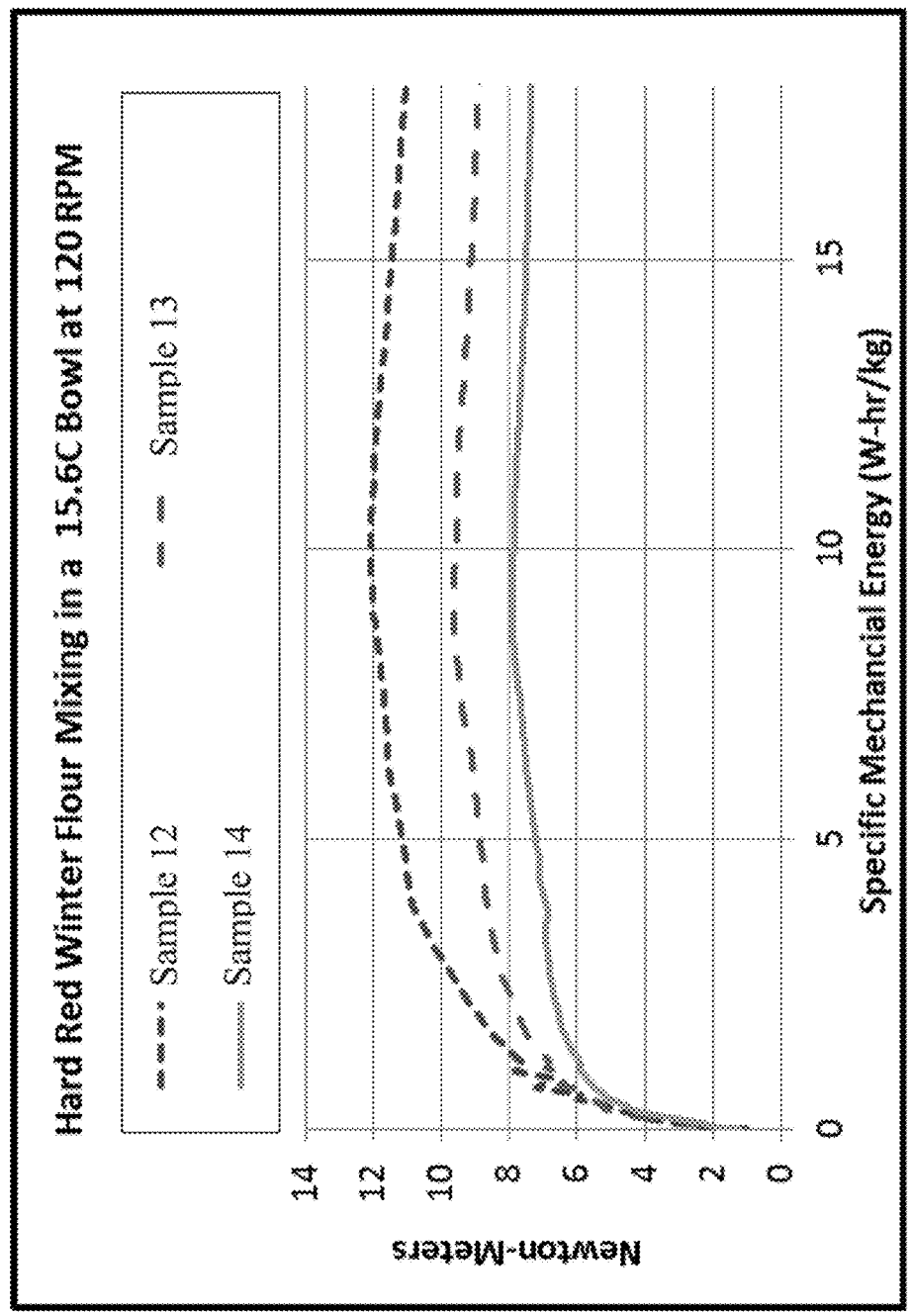

FIG. 12 is a graph of apparent viscosity (in Newton-meters) versus time (in minutes) and FIG. 13 is a graph of apparent viscosity versus specific mechanical energy for Samples 12-14. The development peak for each of Samples 12-14 is at the maximum apparent viscosity.

Figure 14:
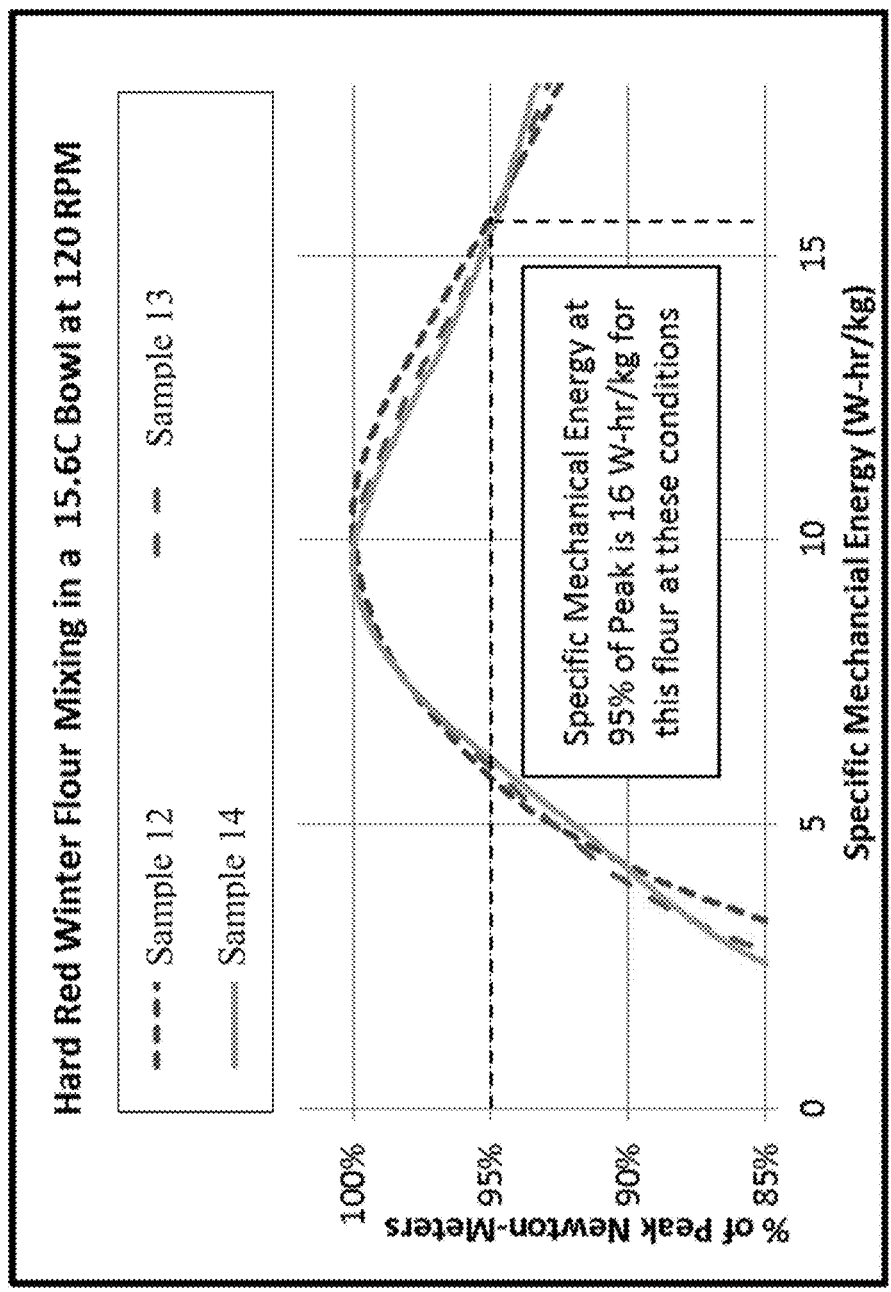

FIG. 14 is a graph of apparent viscosity as a percent of peak versus specific mechanical energy (in W-hr/kg) for Samples 12-14. As shown in FIG. 14, when the protein quality of Samples 12-14 is expressed as apparent viscosity as a percent of peak as a function of specific mechanical energy, the development peak for each sample occurs at 100% of peak viscosity and Samples 12-14 experience similar post-peak behavior.

Samples 15-17 also used the same flour but at different flour to water ratios as summarized in Table 3. Samples 15-17 were mixed with a Farinograph E as described above for Samples 4-7 at a mixing speed of 120 RPM. The mixing bowl of the Farinograph E was maintained at 30° C. during the mixing process.

TABLE 3

|  | Flour (grams) | Water (grams) |
| --- | --- | --- |
| Sample 15 | 307 | 173 |
| Sample 16 | 300 | 180 |
| Sample 17 | 293 | 187 |

Figure 15:
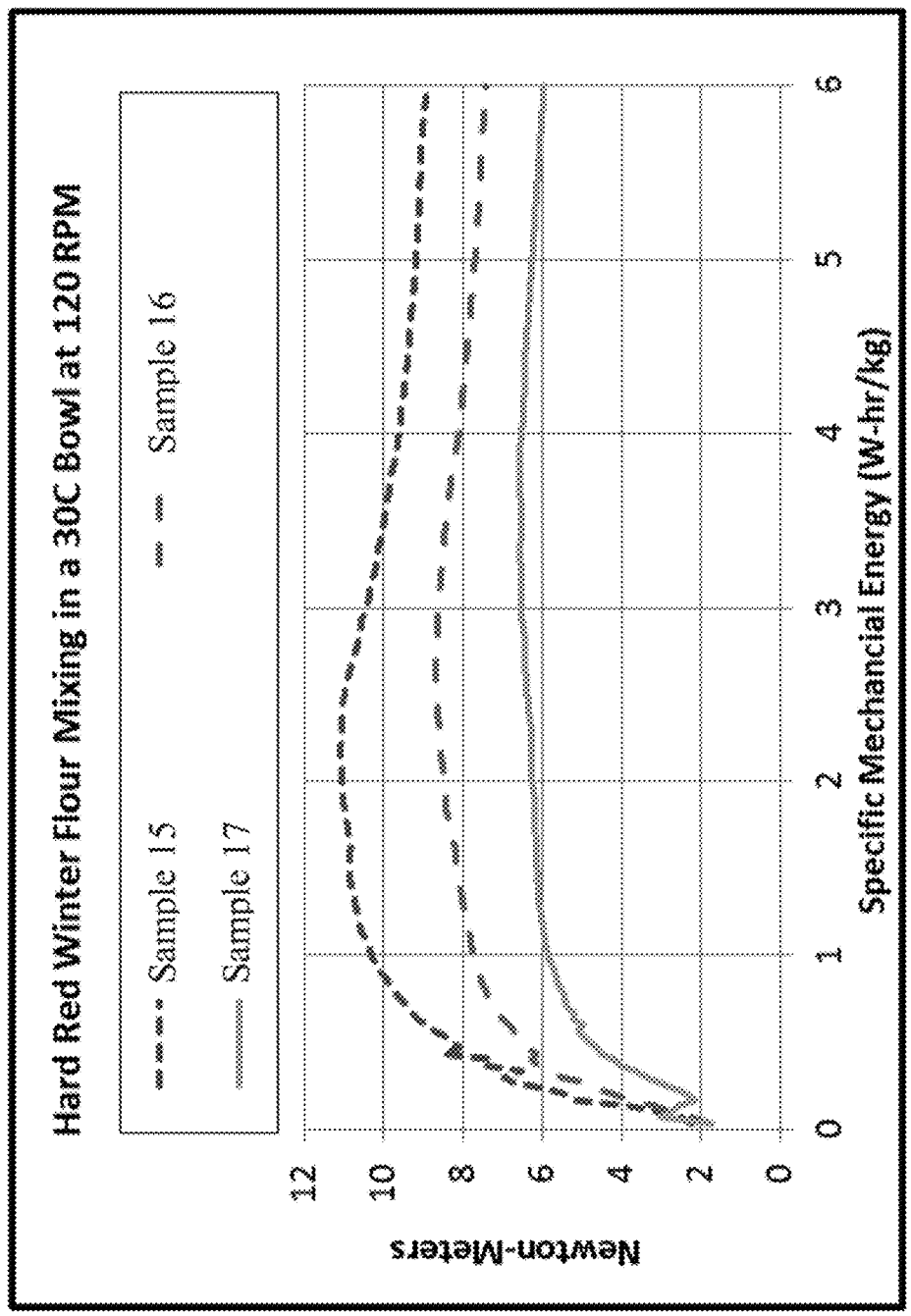
Figure 16:
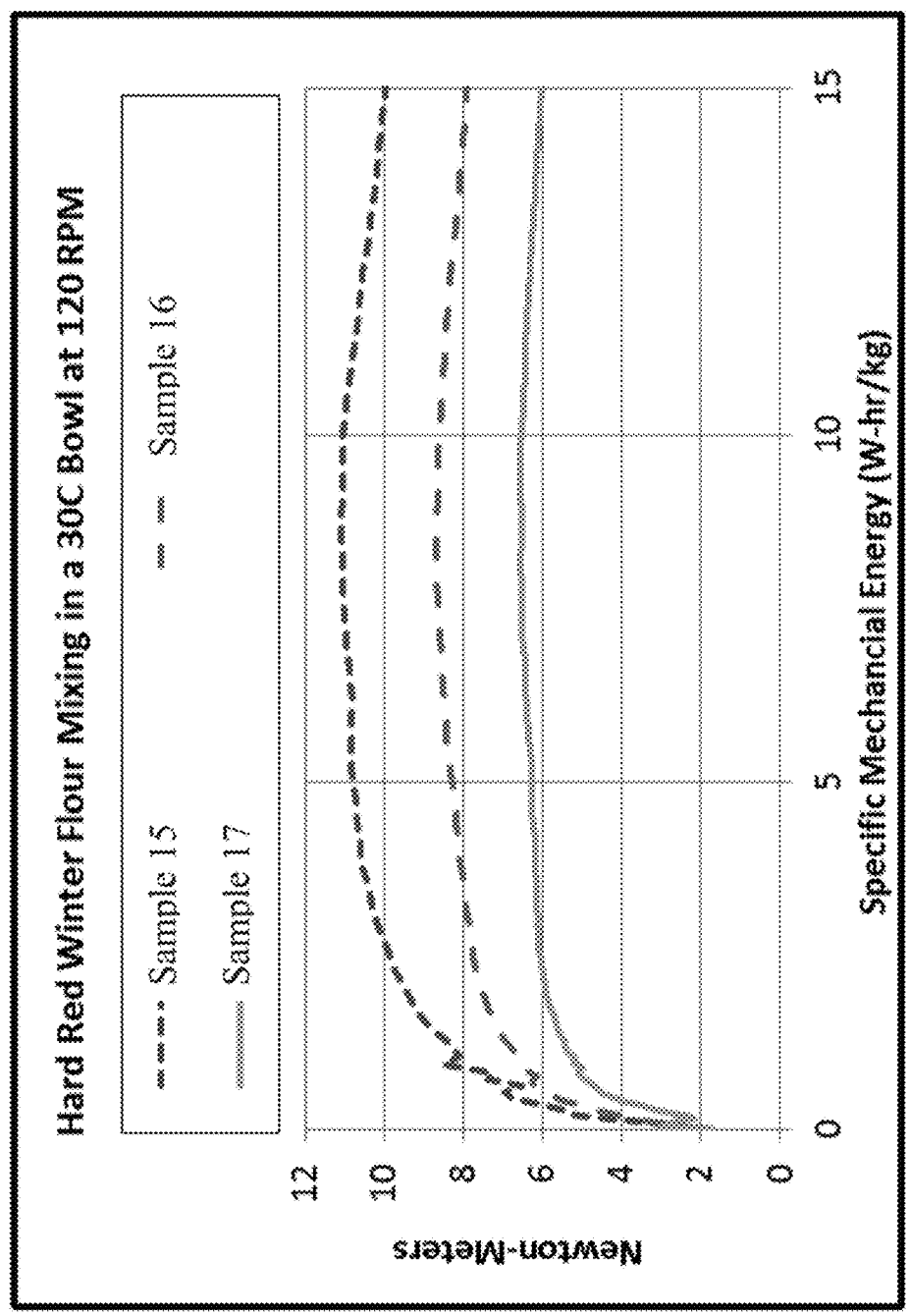

FIG. 15 is a graph of apparent viscosity (in Newton-meters) versus time (in minutes) and FIG. 16 is a graph of apparent viscosity versus specific mechanical energy for Samples 15-17. The development peak for each of Samples 15-17 is at the maximum apparent viscosity.

Figure 17:
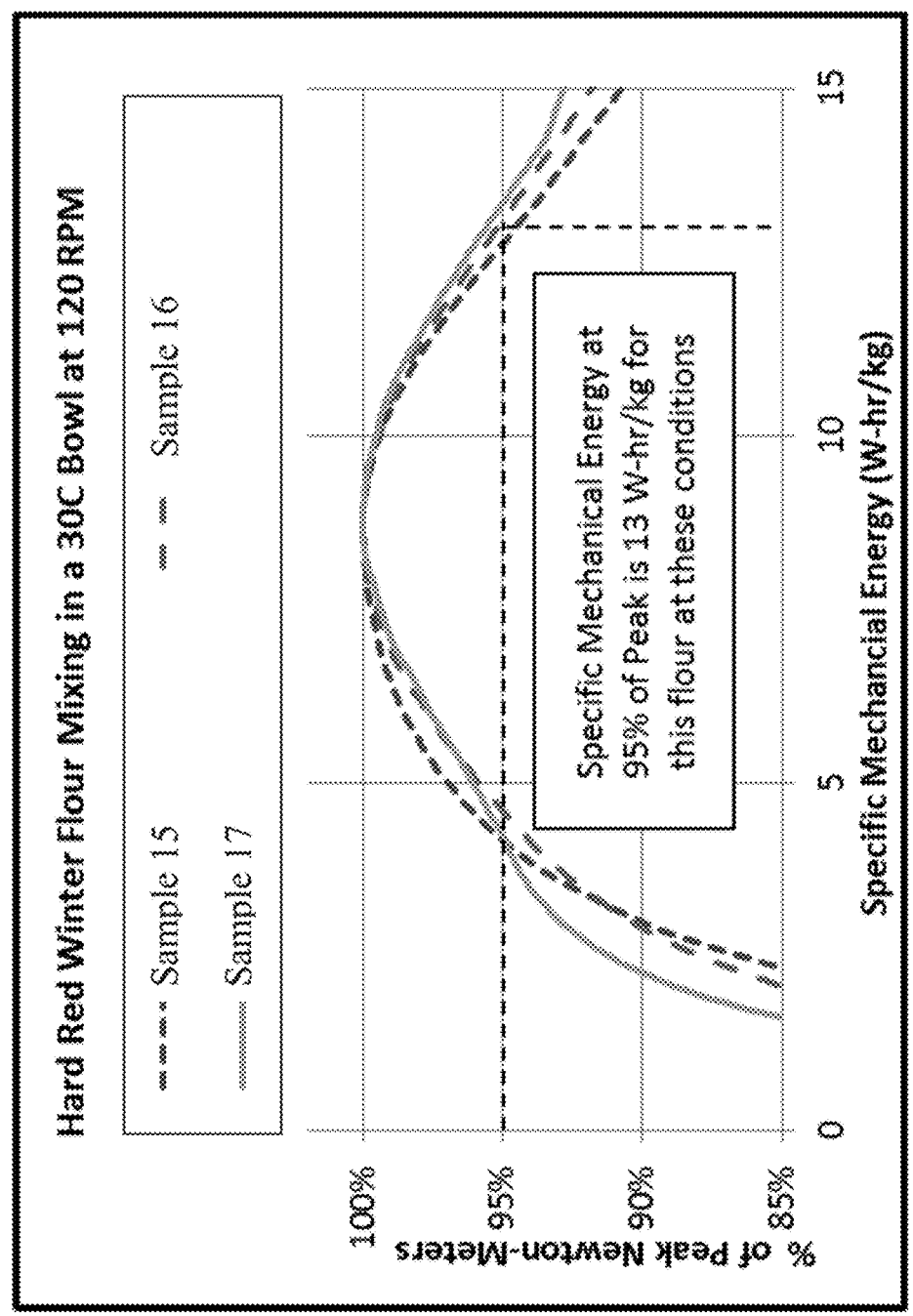

FIG. 17 is a graph of apparent viscosity as a percent of peak versus specific mechanical energy (in W-hr/kg) for Samples 15-17. As shown in FIG. 17, when the protein quality of Samples 15-17 is expressed as apparent viscosity as a percent of peak as a function of specific mechanical energy, the development peak for each sample occurs at 100% of peak viscosity and Samples 15-17 experience similar post-peak behavior.

Samples 18-20 were mixed with a Brabender GlutoPeak. Samples 18-20 used the same flour but at different flour to $CaCl_2$ ratios as summarized in Table 4. Samples 18-20 were mixed at a mixing speed of 1900 RPM, and the mixing bowl of the GlutoPeak was maintained at 34° C. during the mixing process.

TABLE 4

|  | Flour (grams) | 0.5M $CaCl_2$ (grams) |
| --- | --- | --- |
| Sample 18 | 8.5 | 9.5 |
| Sample 19 | 9 | 9 |
| Sample 20 | 9.3 | 8.7 |

Figure 18:
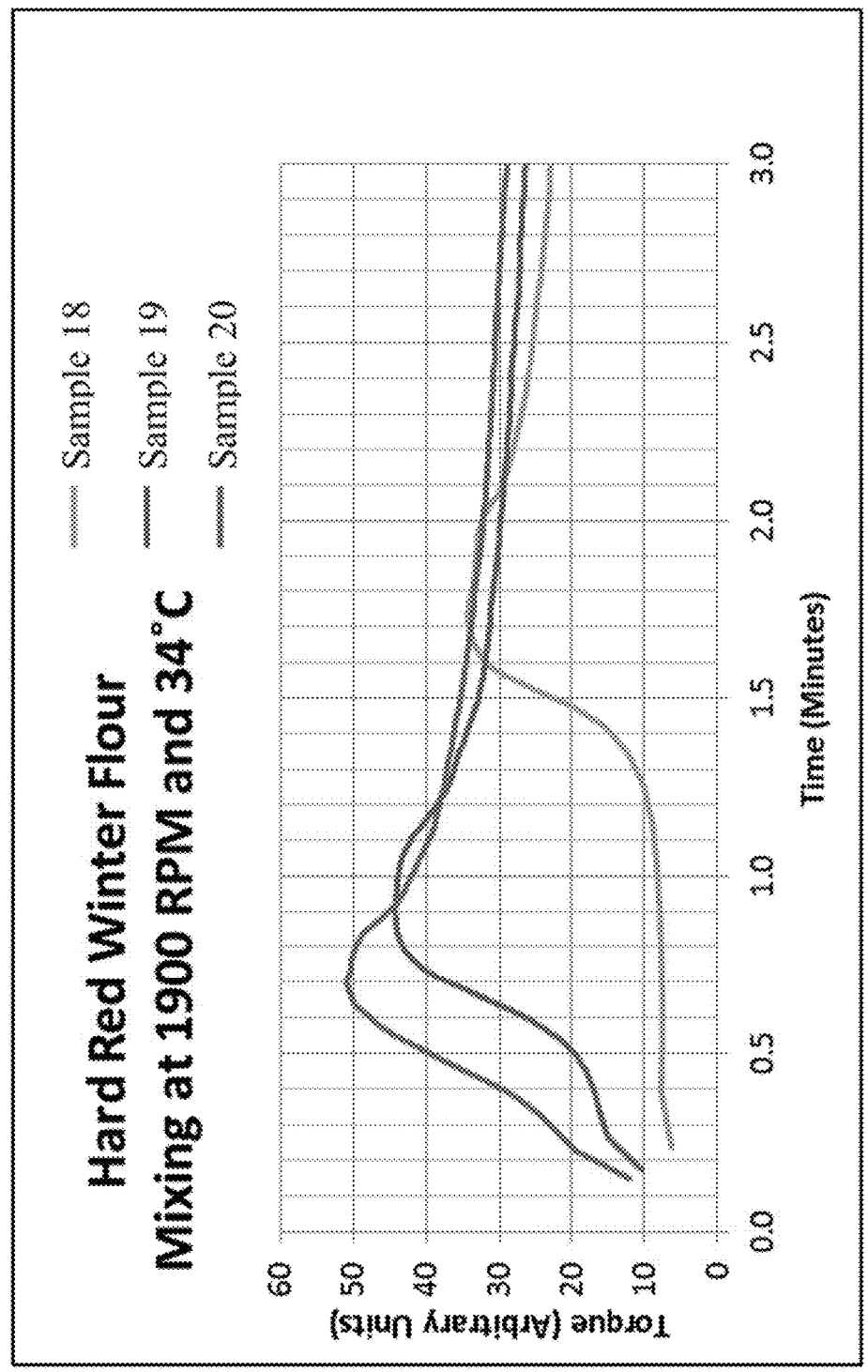
Figure 19:
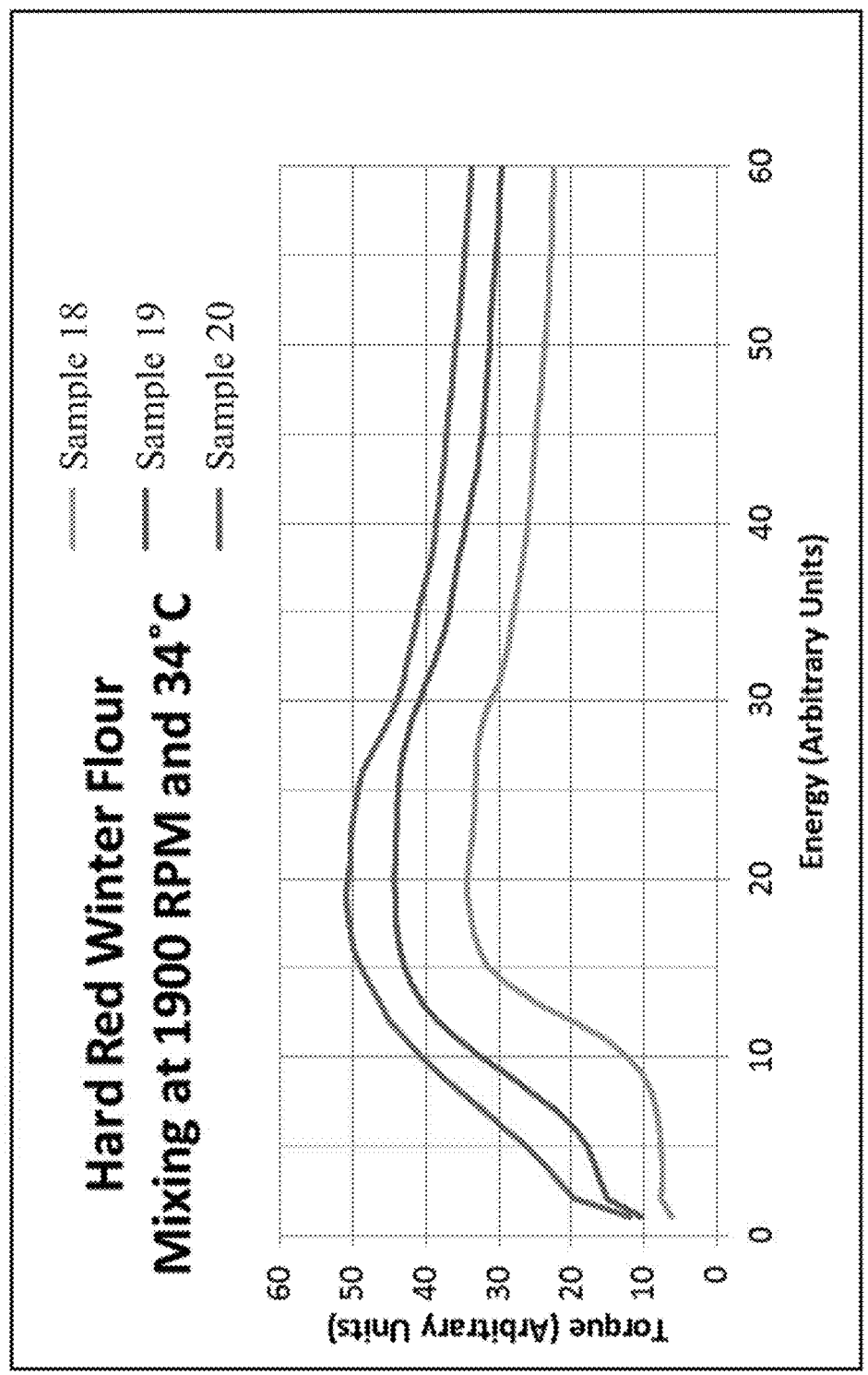

FIG. 18 is a graph of apparent viscosity (in arbitrary units) versus time (in minutes) and FIG. 19 is a graph of apparent viscosity versus specific mechanical energy for Samples 18-20. In FIG. 18 and FIG. 19, the development peak for each of Samples 18-20 is at the maximum apparent viscosity.

Figure 20:
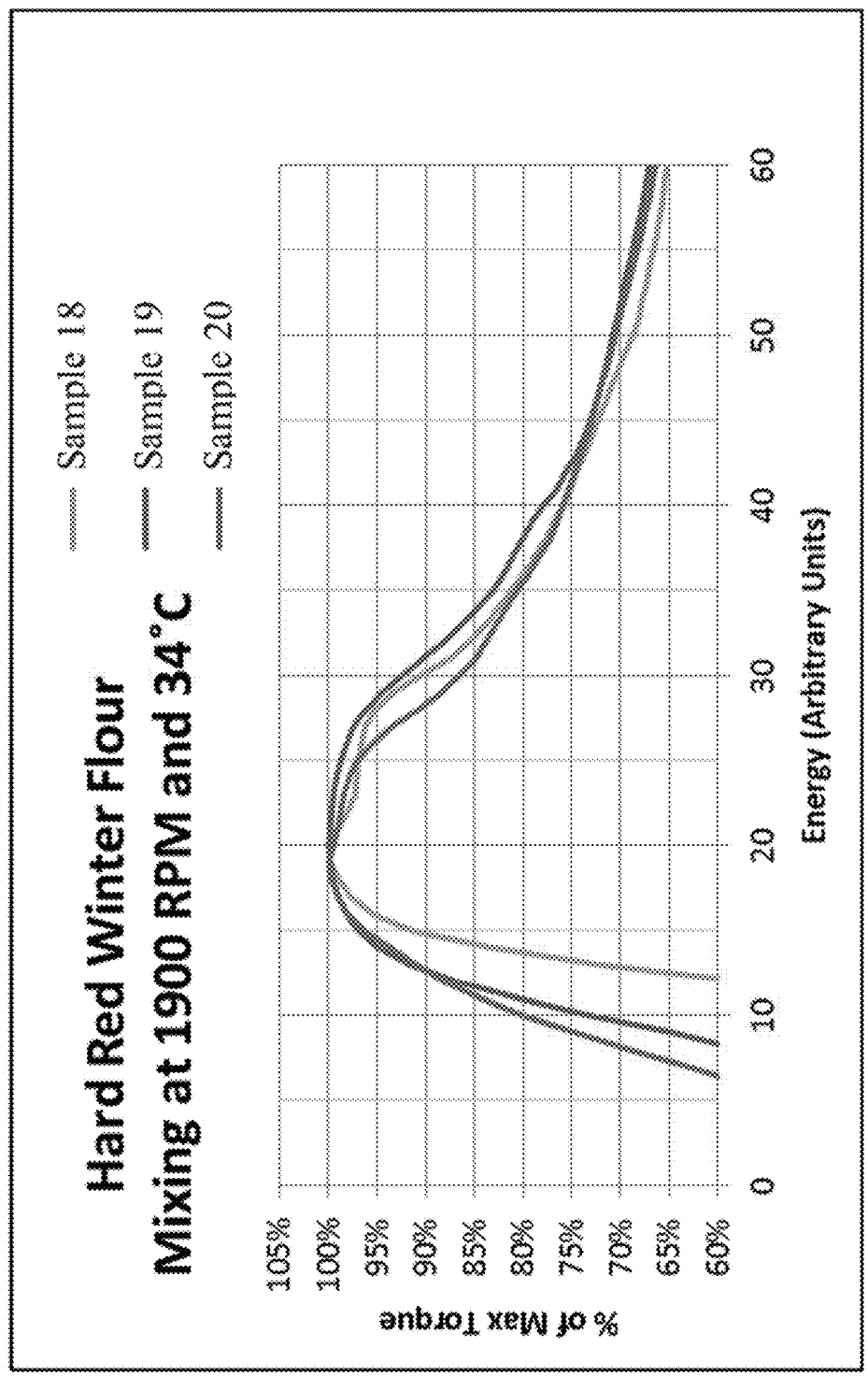

FIG. 20 is a graph of apparent viscosity as a percent of peak versus specific mechanical energy (in W-hr/kg) for Samples 18-20. As shown in FIG. 20, when the protein quality of Samples 18-20 is expressed as apparent viscosity as a percent of peak as a function of specific mechanical energy, the development peak for each sample occurs at 100% of peak viscosity and Samples 18-20 experience similar post-peak behavior.

Samples 21-24 used the same hard red winter flour at different flour to water ratios as summarized in Table 5. Samples 21-24 were mixed with a Farinograph E as described above for Samples 4-7 at a mixing speed of 63 RPM. The bowl of the Farinograph E was maintained at 30° C. during the mixing process.

TABLE 5

|  | Flour (grams) | Water (grams) |
| --- | --- | --- |
| Sample 21 | 316 | 164 |
| Sample 22 | 309 | 171 |
| Sample 23 | 302 | 178 |
| Sample 24 | 295 | 185 |

Figure 21:
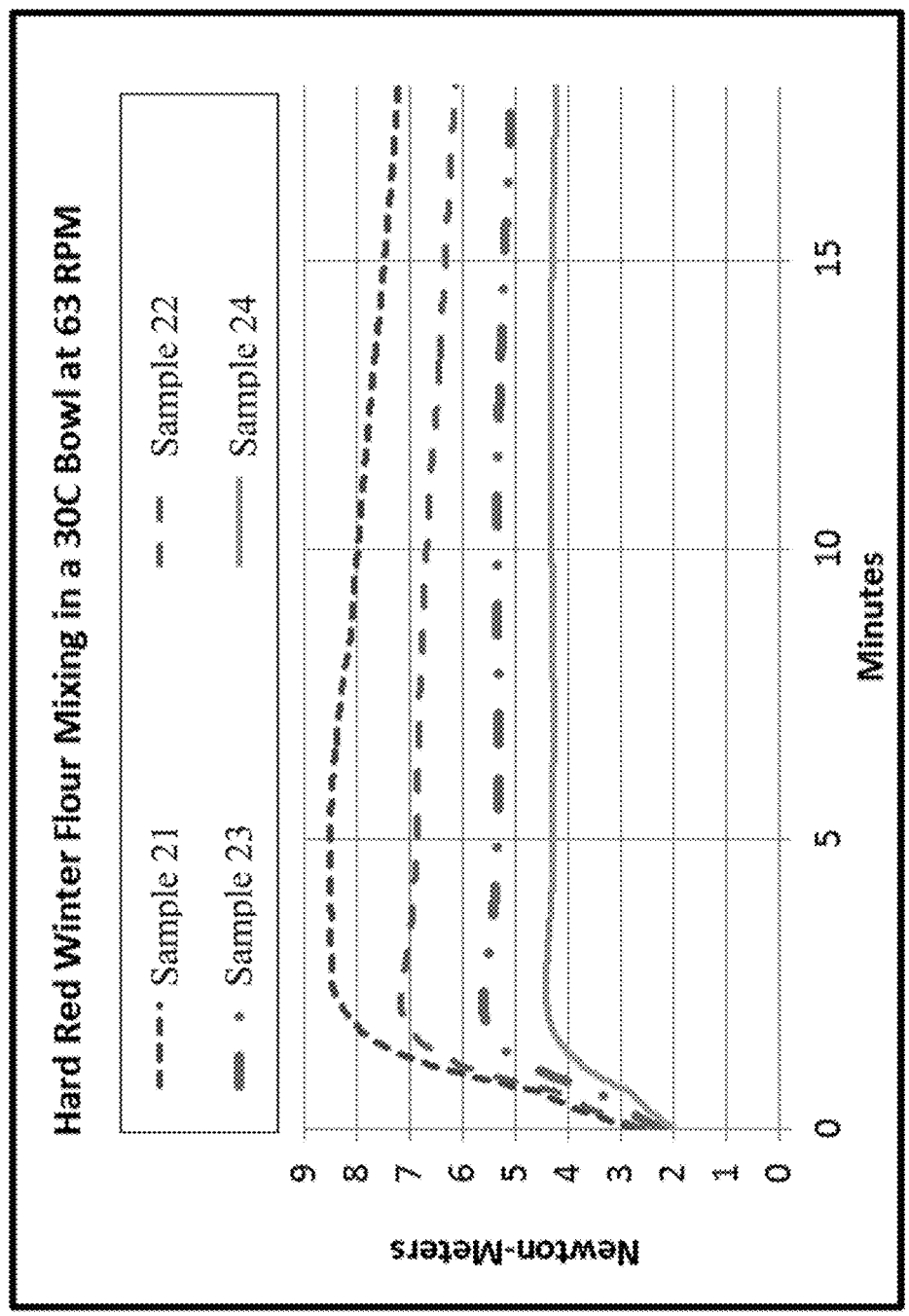
Figure 22:
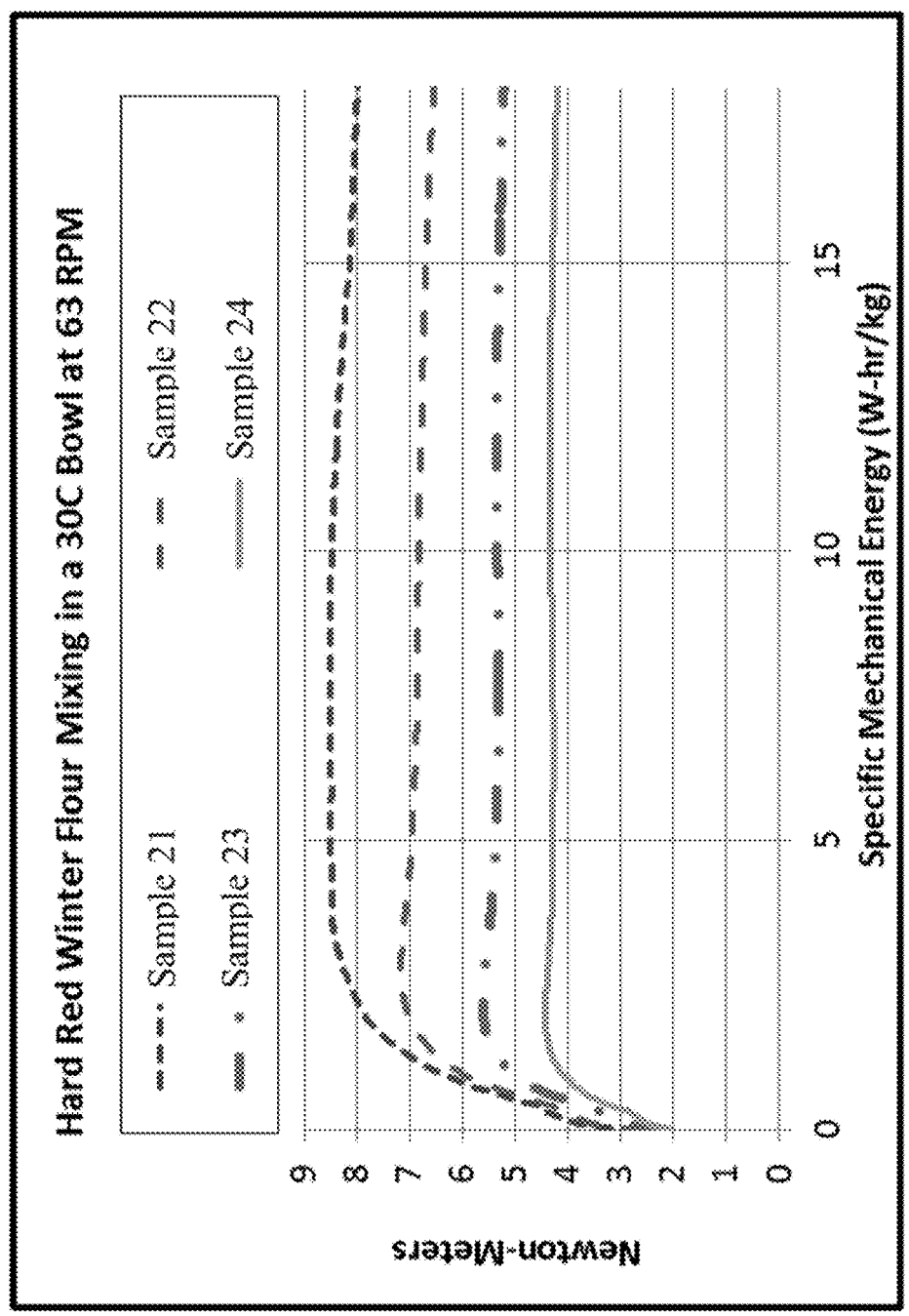
Figure 23:
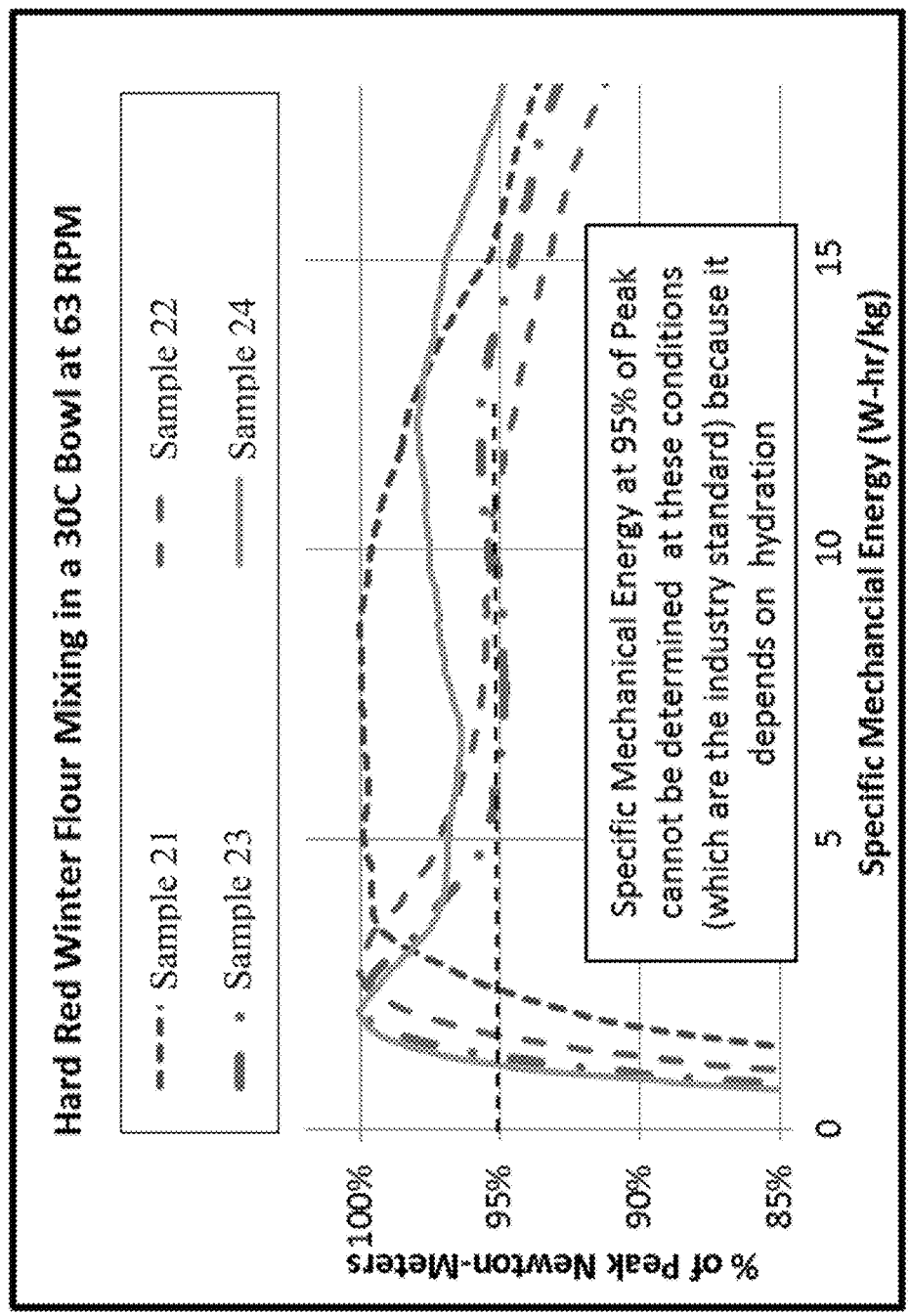

FIG. 21 is a graph of apparent viscosity (in Newton-meters versus time (in minutes)), FIG. 22 is a graph of apparent viscosity versus specific mechanical energy, and FIG. 23 is a graph of apparent viscosity as a percent of peak versus specific mechanical energy for Samples 21-24. As shown in FIG. 23, when expressed as Newton-meters as a percent of peak Newton-meters versus specific mechanical energy, the development peak for each sample does not occur at the same specific mechanical energy for each of Samples 15-17 and these samples do not experience similar post-peak behavior.

Embodiments of the systems, devices, and methods of the foregoing description are optionally employed in a variety of stages of testing, manufacturing and procurement product cycles. For example, some methods relate to a method of procuring flour at a desired flour composition. The method may include communicating a flour composition specification to a milling center, where the flour composition specification relates to a dough test protocol including measuring percent maximum torque of the dough as a function of mechanical energy. Flour is then received from the milling center that is within the flour composition specification.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

We claim:

1. A method for forming a grain composition, the method comprising:
   forming a first grain powder composition comprising at least a first source grain powder;
   mixing at least a portion of the first grain powder composition with water using a mixing apparatus to form a first mixture;
   measuring torque applied to the mixing apparatus by the first mixture at discrete time intervals;
   calculating mechanical energy applied to the first mixture from the measured torque;
   expressing a protein quality of the first grain powder composition as the measured torque as a function of mechanical energy;
   comparing the protein quality of the first grain powder composition to a standard; and
   forming a second grain powder composition having a different weight percent of the first source grain powder than the first grain powder composition if the protein quality of the first grain powder composition does not meet the standard.

2. The method of claim 1 further comprising:
   calculating a viscosity of the first mixture from the measured torque; and
   expressing the protein quality of the first grain powder composition as the viscosity as function of mechanical energy.

3. The method of claim 2 wherein the viscosity is apparent viscosity as a percent of peak apparent viscosity.

4. The method of claim 1 further comprising:
   determining that the protein quality of the first grain powder composition exceeds the standard; and
   forming the second grain powder mixture with a second grain powder and an decreased amount of the first grain powder relative to the first mixture.

5. The method of claim 1 further comprising:
   mixing at least a portion of the second grain powder composition with water using a mixing apparatus to form a second mixture;
   measuring the torque applied to the mixing apparatus by the second mixture at discrete time intervals;
   calculating mechanical energy applied to the second mixture from the measured torque;
   expressing a protein quality of the second grain powder composition as the measured torque as a function of mechanical energy; and
   comparing the protein quality of the second grain powder composition to the standard, wherein the first mixture and the second mixture have the same flour to water ratio.

6. The method of claim 1 wherein the torque is measured before the first mixture reaches a maximum development and after the first mixture reaches a maximum development.

7. The method of claim 1 wherein mixing at least a portion of the first grain powder with water comprises mixing at least a portion of the first grain powder with water in a vessel maintained at 20° C. or less using the mixing apparatus.

8. The method of claim 7 wherein mixing at least a portion of the first grain powder with water comprises mixing at least a portion of the first grain powder with water using the mixing apparatus at 70 revolutions per minute (RPM) or less.

9. The method of claim 1 wherein a steady state temperature of the first mixture during mixing is less than or equal to an average temperature of the first grain powder composition and water before mixing, and the first grain powder composition and water are mixed using the mixing apparatus at 70 revolutions per minute (RPM) or less.

10. The method of claim 1 wherein mixing at least a portion of the first grain powder with water comprises mixing at least a portion of the first grain powder with water in a vessel maintained at 30° C. or less.

11. The method of claim 10 wherein mixing at least a portion of the first grain powder with water comprises mixing at least a portion of the first grain powder and water using the mixing apparatus at 100 revolutions per minute (RPM) or greater.

12. The method of claim 1 wherein the protein quality is determined by the mechanical energy at a percent peak apparent viscosity of less than 100% after maximum development of the mixture.

13. The method of claim 1 and further comprising recording torque as a function of time.

14. The method of claim 1 wherein a steady state temperature of the first mixture during mixing is less than or equal to an average temperature of the first grain powder composition and water before mixing.

15. The method of claim 1 wherein torque is measured for a predetermined time period after the mixture reaches maximum development.

16. The method of claim 1 wherein the mixing apparatus is an electric mixing apparatus.

17. A method of forming a dough, the method comprising:
    forming a grain composition according to claim 1; and
    if the first grain powder composition meets the standard, mixing at least a portion of the first grain powder composition with water and at least one dough component to form a dough.

\* \* \* \* \*